US009725415B2

(12) United States Patent
Pazenok et al.

(10) Patent No.: US 9,725,415 B2
(45) Date of Patent: Aug. 8, 2017

(54) PROCESS FOR THE PREPARATION OF 5-FLUORO-1H-PYRAZOLES

(71) Applicant: BAYER CROPSCIENCE AKTIENGESELLSCHAFT, Monheim am Rhein (DE)

(72) Inventors: Sergii Pazenok, Solingen (DE); Norbert Lui, Odenthal (DE); Christian Funke, Leichlingen (DE); Arnd Neeff, Burscheid (DE); Vadim Mikhailovich Timoshenko, Kiev (UA); Elena Ivanovna Kaminskaya, Kiev (UA); Yuriy Grigorievich Shermolovich, Kiev (UA)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/037,564

(22) PCT Filed: Nov. 25, 2014

(86) PCT No.: PCT/EP2014/075490
§ 371 (c)(1),
(2) Date: May 18, 2016

(87) PCT Pub. No.: WO2015/078846
PCT Pub. Date: Jun. 4, 2015

(65) Prior Publication Data
US 2016/0289194 A1   Oct. 6, 2016

(30) Foreign Application Priority Data
Nov. 27, 2013   (EP) .................................... 13194561

(51) Int. Cl.
C07D 231/16   (2006.01)
C07D 403/04   (2006.01)
C07D 231/14   (2006.01)
C07D 231/38   (2006.01)

(52) U.S. Cl.
CPC ......... *C07D 231/16* (2013.01); *C07D 231/14* (2013.01); *C07D 231/38* (2013.01); *C07D 403/04* (2013.01)

(58) Field of Classification Search
None
See application file for complete search history.

(56) References Cited

U.S. PATENT DOCUMENTS

| 5,254,774 A | 10/1993 | Prokop |
| 8,946,234 B2 | 2/2015 | Maue et al. |
| 2015/0099766 A1 | 4/2015 | Maue et al. |

FOREIGN PATENT DOCUMENTS

| SU | 1456419 A1 | 2/1989 |
| WO | 2005040110 A1 | 5/2005 |
| WO | 2007107470 A2 | 9/2007 |
| WO | 2009089508 A1 | 7/2009 |
| WO | 2010051926 A2 | 5/2010 |
| WO | 2012107434 A1 | 8/2012 |

OTHER PUBLICATIONS

International Search Report from corresponding PCT/EP2014/075491, mailed Mar. 31, 2015.
Chi et al., "Synthesis of fluorinated N-arylpyrazoles with perfluoro-2-methyl-2-pentene and arylhydrazines", Journal of Flourine Chemistry. (Aug. 10, 1999) vol. 28, No. 1: 29-36.
Bergamova et al., "5-Fluoro-Substituted Pyrazoles" Bulletin of the Academy of Sciences of the USSR. (Jan. 1, 1991) vol. 39, No. 11: 2338-2344.
Becer et al.; "Click Chemistry Beyond Metal-Catalyzed Cycloaddition"; Angew. Chem. Int. Ed. 2009; vol. 48; pp. 4900-4909.
Bock et al.; "Cul-Catalyzed Alkyne-Azide "Click" Cycloadditions from a Mechanistic and Synthetic Perspective"; Eur. J. Org. Chem. 2006; pp. 51-68.
Konig et al.; "Eine neue Methode zur Synthese von Peptiden: Aktivierung der Carboxylgruppe mit Dicyclohexylcarbodiimid unter Zusatz von 1-Hydroxy-benzotriazolen"; Chem. Ber. 103; 1970; pp. 788-798.
Chi et al.; "Synthesis of fluorinated N-arylpyrazoles with perfluoro-2-methyl-2-pentene and arylhydrazines"; Journal of Fluorine Chemistry; vol. 98; No. 1; 1999; pp. 29-36.
Houben-Weyl; "Umwandlung von Carbonsauren"; vol. VIII; 1952; pp. 463-483.
Anderson et al.; "A Reinvestigation of the Mixed Carbonic Anhydride Method of Peptide Synthesis"; Journal of American Chemical Society; Sep. 13, 1967; pp. 5012-5017.
Williams et al.; Development of a Novel Class of Cyclic Hexapeptide Oxycotin Antagonists Based on a Natural Product; J. Med. Chem.; vol. 35; 1992; pp. 3905-3918.
Spivey et al.; Solid-Phase Synthesis of an A-B Loop Mimetic of the Ce3 Domain of Human IgE: Macrocyclization by Sonogashira Coupling; J. Org. Chem.; vol. 68; 2003; pp. 1843-1851.
Perlow et al.; Use of N-Fmoc Amino Acid Chlorides and Activated 2-(Fluorenylmethoxy)-5(4H)-oxazolones in Solid-Phase Peptide Synthesis; Efficient Synthese of Highly N-Alkylated Cyclic Hexapeptide Oxytocin Antagonists Related to L-365; J. Org. Chem.; vol. 57; 1992; pp. 4394-4400.
Brunskill et al.; "Anionic Oligomerisation of Hexafluoropropene: Fission of a Carbon-Carbon Bond by Fluoride Ion"; Journal of the Chemical Society; vol. 21; 1970; pp. 1444-1446.
Knunyants et al.; Izv. Akad. Nauk; SSSR; 1990; pp. 2583-2589.
Lutz; "Copper-Free Azide-Alkyne Cycloadditions: New Insights and Perspectives"; Angew. Chem. Int. Ed.; vol. 47; 2008; pp. 2182-2184.
Martini et al.; "Uber die Umsetzung von Hexafluorpropen und Perfluor-2-methyl-2-penten mit Wasser"; Journal of Fluorine Chemistry; vol. 8; 1976; pp. 535-540; XP002727522.

(Continued)

*Primary Examiner* — Kamal Saeed
(74) *Attorney, Agent, or Firm* — McBee Moore Woodward Vanik IP, LLC

(57) ABSTRACT

A new process for the preparation of 5-fluoro-1H-pyrazoles of the general formula (I) as described herein, resulting from the reaction of an olefin with hydrazine in the presence of water and a base.

15 Claims, No Drawings

(56) References Cited

OTHER PUBLICATIONS

Sakya et al.; "Efficient Synthesis of 5-alkyl Amino and Thioether Substitued Pyrazoles"; Tetrahedron Letters; vol. 44; 2003; pp. 7629-7632.

Snegirev et al.; "Reaction of Secondary Amines with Hexafluoropropylene Dimers"; Plenum Publishing Corporation; 1984; pp. 2305-2312 and English Translation; pp. 106-119.

Bergamova et al.; "Bulletin of the Academy of the USSR, Division of Chemical Sciences"; Springer New York; vol. 39; No. 11; pp. 2338-2344.

PROCESS FOR THE PREPARATION OF 5-FLUORO-1H-PYRAZOLES

CROSS REFERENCE TO RELATED APPLICATIONS

This application is a §371 National Stage Application of PCT/EP2014/075490, filed 25 Nov. 2014, which claims priority to EP 13194561.0, filed 27 Nov. 2013.

BACKGROUND

Field of the Invention 5-fluoro-1H-pyrazoles, in particular 5-Fluoro-1-methyl-3-pentafluoroethyl-4-trifluoromethyl-1H-pyrazole, are important building blocks for the preparation of crop protection chemicals, as those described in WO 2010051926.

Description of Related Art

It is known that 5-fluoro-1-methyl-3-pentafluoroethyl-4-trifluoromethyl-1H-pyrazole can be prepared by the treatment of the dimer of hexafluoropropene with water free N,N-dimethylhydrazine in diethyl ether at −50° C. followed by heating of the intermediate at 120° C., I. L. Knunyants et al. Izv. Akad. Nauk SSSR, (1990) 2583-2589.

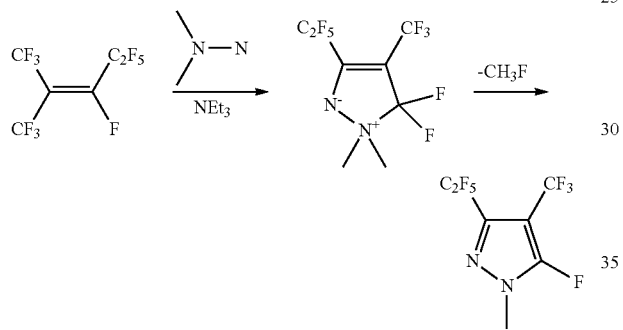

However, this two step transformation requires low temperatures for the first step and results in the formation of $CH_3F$ during the thermal elimination in the second step, making this process expensive, environmentally unfriendly, and particularly difficult for industrialization.

Starting from perfluoro-2-methyl-2-penten and phenylhydrazine, in the presence of triethylamine at −50° C. 1-Phenylpyrazole has been shown to be obtainable in 90% yield (SU 1456419). Furin et al. J. Fluor. Chem. 98(1999) 29 reported that the reaction of perfluoro-2-methyl-2-pentene with phenylhydrazine in $CH_3CN$ gave a mixture of isomeric pyrazoles 3 and 4 in a ratio 4:1.

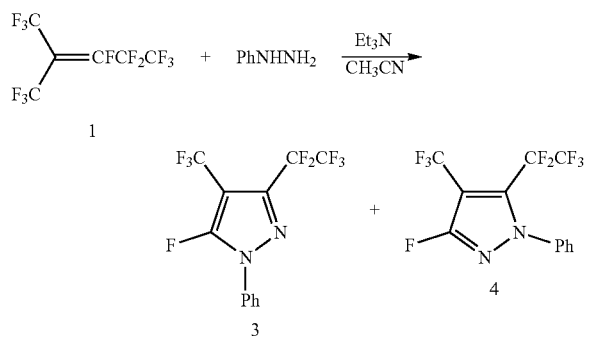

Although, commercially available at low cost (especially in the form of their water solutions) the use of monoalkylhydrazines for the regioselective synthesis of the said pyrazoles is not known from the prior art. The problem to be solved by this invention was to identify a simple and selective process for preparing 5-fluoro-1H-pyrazoles from available fluoroalkenes and mono-substituted hydrazines, which should in particular be amenable for an industrial scale process. As an additional advantage, this process should have a favorable profile with respect to safety and production of unwanted waste material.

SUMMARY

Surprisingly, 5-fluoro-1H-pyrazoles of the general formula (I)

can be prepared in high purity and in a short and simple process by reacting an olefin of the general formula (a)

with water, followed by reaction with hydrazines of Formula (b)

$$R^1\text{---NH---}NH_2 \quad (b)$$

wherein
$R^1$ is selected from $C_1$-$C_6$ alkyl, cycloalkyl, $C_5$-$C_{10}$ aryl;
$R^2$ is a trihalomethyl moiety with at least one fluorine atom; and
$R^3$ is selected from $C_1$-$C_5$ haloalkyl as $CF_3$, $CF_2Cl$, $C_2F_5$, $C_3F_7$, $CF_2CF_2Cl$, $CFClCF_3$ Surprisingly, is has been found that the interaction of fluoroalkenes of formula (a) in a first step with water and a base, followed by a reaction of the formed intermediates of formula (c) with hydrazines of formula (b) proceeds regioselectively with the formation of only or almost only one isomeric pyrazole of the formula (I) in a high yield.

DETAILED DESCRIPTION OF A PREFERRED EMBODIMENT

The process according to the invention is illustrated in the following two step diagram:

Step 1: Reaction of Compounds of Formula (II) with Water and a Base

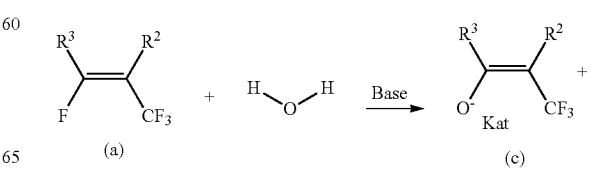

Typically Kat depends on the choice of the base used in the reaction. Preferably, Kat is selected from $Li^+$, $Na^+$, $K^+$, $Cs^+$, $(NAlkyl_4)^+$, $(HNAlkyl_3)^+$. Most preferable, Kat is $(HNAlkyl_3)^+$.

A method of preparing the compound of formula (c) is described in: V. Snegirev et all Izvestiya Akademii Nauk SSR, Seriya Khimicheskaya, N. 1, pp. 106-119, 1986 and T. Martini, J. Fluor. Chem., 8, 1976, 535-540.

The reaction can be performed in the presence of organic and inorganic bases. Preferred organic bases to carry out the reaction are: trimethylamine, triethylamine, tripropylamine, tributylamin, methydiisopropylamin, N-methylmorpholine, pyridine, alkylpyridines, trimethybenzylammonium hydroxide, tetrabutylalammonim hydroxide, Hünig base. Preferably base is triethylamine.

Preferred inorganic bases to carry out the reaction are: $NaHCO_3$, $K_2CO_3$, NaOH, $NaHCO_3$, KF, LiOH, CsOH, $Cs_2CO_3$.

According to a further preferred embodiment of the present invention, the amount of water used in the reaction is in the range of 1 to 10 equivalents, preferably in the range of 1.2 to 7 equivalents, more preferably between 1 to 5 equivalents per one equivalent of compound of formula (a).

The amount of base is in the range of 1 to 7 equivalents, preferably between 1.5 to 5 equivalents, more preferably between 1.5 to 3.5 equivalents per one equivalent of the compound of formula (a).

Generally, the reaction time for the performance of step 1 is not of critical importance and can inter alia depend on the reaction volume, nature of the base employed, and the reactivity of the alkene of formula (a). Preferably it is within the range of 1 to 5 h, more preferably within the range of 1 to 3 h.

Step 2: Reaction of Compounds of Formula (c) with Hydrazines of Formula (b)

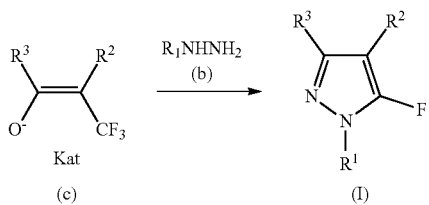

It is essential for the performance of the invention that compound (c) exists under conditions that prevent its isomerization or decomposition, for instance by formation of the corresponding ketone, via e.g. acidification. This is typically ensured by the control of the pH or the choice of a proper base to stabilize the compounds of formula (c).

Kat is a kation except from a proton. Typically, any organic or inorganic kation other than a proton can be used in the reaction.

Preferably $R^1$ is selected from alkyl, particularly preferably it is methyl.

Preferably $R^2$ is selected from $CF_3$, $CF_2Cl$, particularly preferably it is $CF_3$.

Preferably $R^3$ is selected from $CF_3$, $C_2F_5$, $C_3F_7$, $CF_2CF_2Cl$, $CFClCF_3$, particularly preferably it is, $C_2F_5$.

Most preferable is the combination of $R^1$=methyl, $R^2$=$CF_3$, $R^3$=$C_2F_5$.

A preferred embodiment of the present invention relates to a process for preparing pyrazoles of formula (Ia),

wherein $R^1$ is selected from $C_1$-$C_6$ alkyl, and which comprises the reaction of perfluoro-2-methyl-2-pentene

with a hydrazine of general formula (b).

Monoalkylhydrazines and Monoarylhydrazines are commercially available.

A particularly preferred embodiment of the present invention relates to a process for preparing pyrazoles of formula (Ib), starting from perfluoro-2-methyl-2-pentene

Perfluoro-2-methyl-2-pentene is commercially available (Fa. Daikin) and P&M Invest (Russia) or can be prepared via dimerization of hexafluoropropene, see U.S. Pat. No. 5,254,774; R. Haszeldiner et al, Journal of the Chemical Society [Section] D: Chemical Communications (1970), (21), 1444-1445.

Preferred compounds of formula (c) are

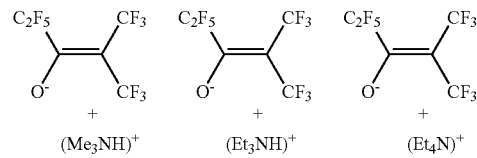

The cyclisation reaction (step 2) is performed in different solvents selected from
a) alkanes, like hexanes e.g. cyclohexane or methylcyclohexane;
b) haloalkanes, preferably dichlorometane, dichlorethane;
c) alcohols, preferably methanol, ethanol, or isopropanol;
d) nitriles, preferably acetonitrile, or butyronitrile;
e) amides, preferably dimethylformamide, or dimethylacetamide;
f) ethers like diethylether, methyltert.butylether, dimethoxyethane, diglym,
g) benzene, toluene, dichlorobenzene, chlorobenzene.

Particularly preferred solvents for the cyclisation are dichloromethane, dichloroethane, acetonitrile and butyronitrile, most preferred solvents for this reaction are dichloromethane, acetonitrile and butyronitrile. According to a further embodiment of the present invention, the cyclization is performed at temperatures ranging from −5° C. to 50° C., more preferably at temperatures ranging from 0° C. to 30° C., most preferably from 0° C. to room temperature.

Generally, the reaction time is not of critical importance and can depend on the reaction volume, preferably it is within the range of 3 to 20 h, more preferably within the range of 1 to 5 h.

The ratio of the compound of formula (IV) and the compound of formula (III) can vary within a large range, preferably it is within 0.9 to 3.5 equivalents, more preferably between 1 to 2.5 equivalents, even more preferably between 1 to 1.5 equivalent of (III) per one equivalent of the compound of formula (IV).

Step 3

In a Step 3, the compound of formula (I), preferably compound (Ia), can be transformed into its CN analog of formula (6) or (6a), respectively

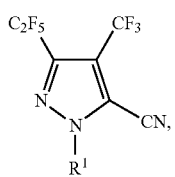

(6)

wherein $R^1$ is $(C_1$-$C_4)$-alkyl, preferably, a compound of formula (6) is a compound of formula (6a):

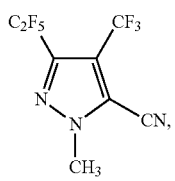

(6a)

by reacting compound (I), preferably compound (Ia), with a CN-donor such as alkaline cyanides (e.g., NaCN, KCN, CsCN, or CuCN).

Typical solvents are acetonitrile, DMF, DMA, N-methylpyrrolidone (NMP), Sulfolan, dimethoxyethane, diglym. Preferred solvents are acetonitrile, DMF or DMA.

Typically, the temperature for this reaction is between 30° C. and 120° C., preferably between 40° C. and 110° C., more preferably above 60° C. such as between 60° C. and 120° C. or between 60° C. and 100° C.

Generally, the reaction time is not of critical importance and can depend on the reaction volume. Preferably, the reaction time is between 2 h and 8 h, more preferably between 4 and 8 h.

Step 4

In a Step 4, a compound of formula (6), preferably (6a), can be transformed in its carboxylic acid analog of formula (7), preferably formula (7a), respectively, according to hydrolysis steps known in the art:

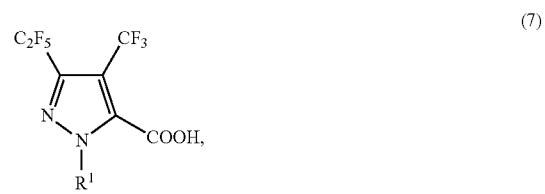

(7)

wherein $R^1$ is $C_1$-$C_4$-alkyl, preferably a compound of formula (7) is a compound of formula (7a):

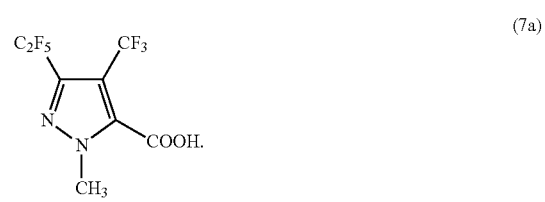

(7a)

The conversion of a cyano group (—CN) into a carboxylic group (—COOH) is generally performed under acidic or basic conditions.

For acidic hydrolysis, preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$. To generate the protonated acidic form of formula (7) or (7a), respectively, a following step of acidification should follow.

Typically, suitable inorganic acids for performing the acidification after completion of the basic hydrolysis is any acid which is stronger than the deprotonated form of a compound of formula (7) or (7a), respectively. Preference is given to mineral acids, for example $H_2SO_4$, HCl, HF, HBr, HI, $H_3PO_4$ or organic acids, for example $CF_3COOH$, p-toluenesulphonic acid, methanesulphonic acid, trifluoromethanesulphonic acid. Preferred acids for this acidifications are HCl or $H_2SO_4$.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile;

amides we dimethylformamide (DMF) or N-methylpyrrolidone or mixtures of such solvents, particular preference being given to water, acetonitrile, dichloromethane and alcohols (ethanol) Preferably, the reaction is carried out in water. The process step of the invention is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours such as between 1 h and 30 h, preferably between 3 h and 20 h.

Preference is given to conversion by means of basic hydrolysis followed by an acidification.

The process step of the invention is performed preferably within a temperature range from 20° C. to 150° C., more preferably at temperatures of 30° C. to 110° C., most preferably at 30° C. to 80° C.

Generally the reaction time may, according to the batch size and the temperature, be selected within a range between 1 hour and several hours such as between 1 h and 30 h, preferably between 3 h and 20 h.

Compounds of Formula (II)

The present invention also refers to a process to produce an insecticidal compound of formula (II), preferably of formula (II'), more preferably of formula (IIa), based on the preparation of compounds of formula (I), more preferably of formula (Ib). Compounds of formula (II) are, e.g., known from WO 2010/051926.

pentafluoroethoxy, preferably hydrogen, fluorine, chlorine, bromine, most preferably chlorine; and $A_2$ is C—$R^3$ or nitrogen; and $R^3$ is hydrogen, methyl, fluorine or chlorine, preferably hydrogen; and Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—$CH_2$—$C_6H_5$);

preferably, a compound of formula (II) is a compound of formula (II'):

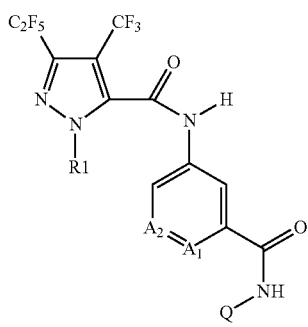

(II)

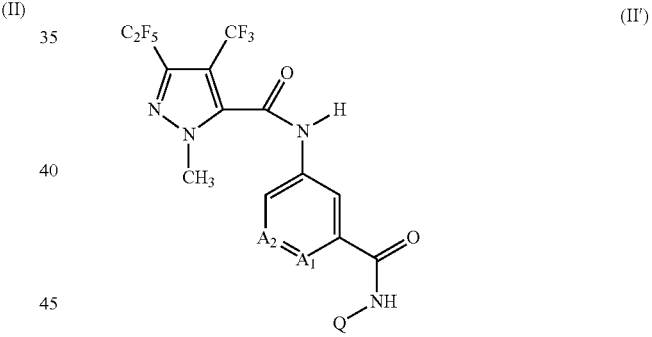

(II')

wherein $R^1$ is $C_1$-$C_4$-alkyl, preferably methyl; and $A_1$ is C—$R^2$; and $R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(═O)—NH-cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or wherein $A^1$ and $A^2$ and Q are as defined for a compound of formula (II), characterized in that the process comprises steps 1 and 2 as described above.

In one preferred embodiment, the compound of formula (II) is compound (IIa) defined by the following substituents:

| $R^1$ | $A_2$ | $A_1$ | Q |
|---|---|---|---|
| $CH_3$ | C—H | C—Cl | Benzyl |

The new and inventive process for preparing a compound of formula (II), preferably (II'), more preferably (IIa), is characterized in that the process comprises steps 1 and 2 as described above. In one preferred embodiment, the process is characterized in that it comprises steps 1 and 2 as described above. In another preferred embodiment, the process comprises in addition to steps 1 and 2 as described above optionally Step 3 and Step 4 as described above and optionally, by the subsequent Step 6 described below.

Optionally, compound (8) in Step 6 can be produced by the reaction indicated in Step 5 which is described below:

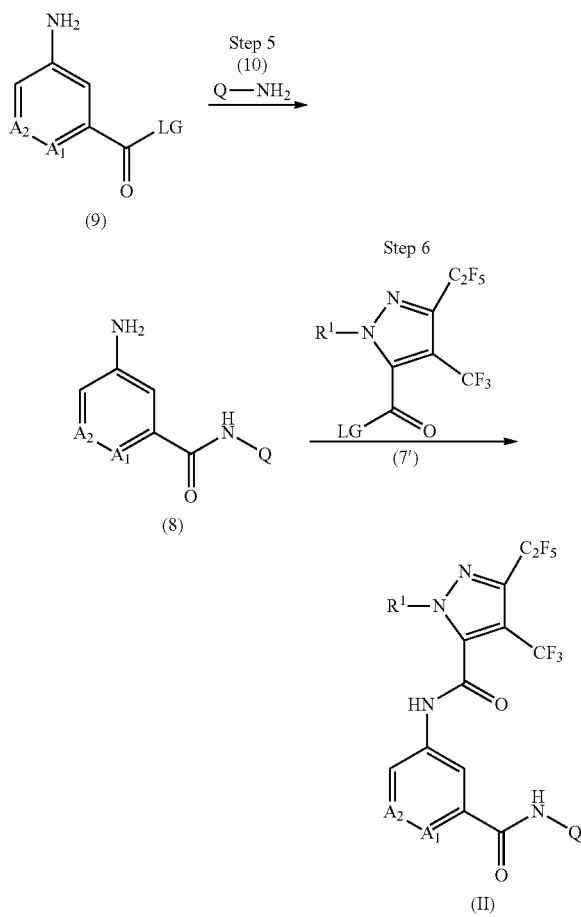

wherein $R^1$ and $A_1$ and $A_2$ and Q have the meanings described for compounds of formula (II). LG is any desired leaving group, e.g. halogen or anhydrate.

Typically, an amine derivative of the formula (8) does not only refer to the amine but also to its salt form (8) $H^+W^-$ wherein $W^-$ is selected from $^-$, $Cl^-$, $Br^-$, $J^-$, $HSO_4^-$, $CH_3COO^-$, $BF_4^-$, $CH_3SO_3^-$, Toluensulphonic acid, $CF_3COO^-$ or $CF_3SO_3^-$.

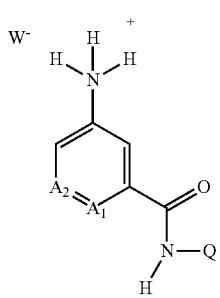

wherein $W^-$ is selected from $^-$, $Cl^-$, $Br^-$, $J^-$, $HSO_4^-$, $CH_3COO^-$, $BF_4^-$, $CH_3SO_3^-$, Toluensulphonic acid, $CF_3COO^-$ or $CF_3SO_3^-$.

Thus, one preferred embodiment refers to the reaction of Step 6 wherein the compound of formula (8) is present in its salt form (8) $H^+W^-$, wherein $W^-$ is selected from $^-$, $Cl^-$, $Br^-$, $J^-$, $HSO_4^-$, $CH_3COO^-$, $BF_4^-$, $CH_3SO_3^-$, Toluensulphonic acid, $CF_3COO^-$ or $CF_3SO_3^-$.

In one more preferred embodiment, a compound of formula (8) is compound (8a) and/or its salt (8a'):

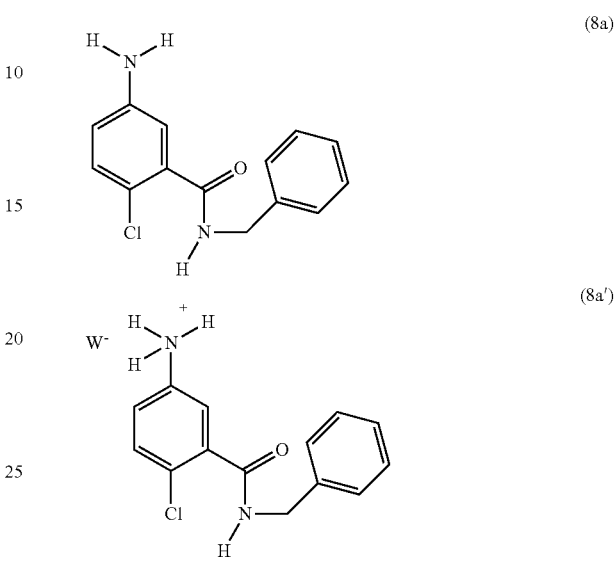

wherein
$W^-$ (in the case of compound (8a')) is selected from the group consisting of $F^-$, $Cl^-$, $Br^-$, $J^-$, $HSO_4^-$, $CH_3COO^-$, $BF_4^-$, $CH_3SO_3^-$, Toluensulphonic acid, $CF_3COO^-$ or $CF_3SO_3^-$.

Step 6

In Step 6, compounds according to the invention of the type (II), preferably (II'), more preferably (IIa), can be synthesized by reacting amines of the general structure (8) (or their salts) with intermediate (7') which is an activated form of carboxylic acid derivative of formula (7), preferably of formula (7a). The reaction can be carried out with or without solvents. In this step, a suitable base can likewise be used.

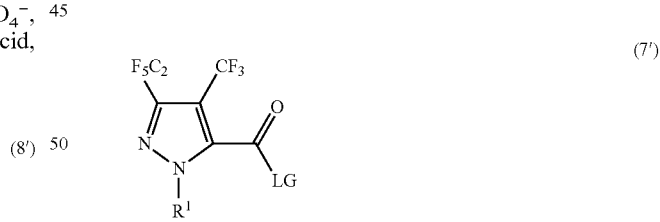

wherein $R^1$ is hydrogen, optionally halogenated $C_1$-$C_4$-alkyl or optionally halogenated cyclopropyl, preferably methyl.

An activated form of carboxylic acid derivative of formula 7, preferably formula (7a), which is indicated in the reaction scheme of Step 6 above by having any leaving group LG in the —C(=O)LG group, encompasses a) analogs of formula (7) or (7a), respectively, wherein the OH of the COOH group is replaced by a suitable leaving group such as halogen; b) anhydrates of compounds of formula (7) or (7a), respectively; or c) compounds of formula (7) or (7a), respectively in the presence of a coupling reagent which presence activates the compound of formula (7) or (7a), respectively, in the sense of the present invention, such as dicyclohexylcarbodiimide or 1-hydroxybenzotriazole. The skilled person is aware of suitable leaving groups preparation of anhydrates of a carboxylic acid or suitable coupling reagents for acid/amine reactions and the preparation of such compounds. Preferred leaving groups are carboxylic acid halides such as carboxylic acid chlorides or fluorides.

Cyclic carboxylic acid halides, as inter alia represented by the general structure (7'), can be prepared simply by reacting a heterocyclic carboxylic acid of compound (7) with halogenating reagents such as thionyl chloride, thionyl bromide, phosphoryl chloride, oxalyl chloride, phosphorus trichloride, etc. (Houben-Weyl (1952) vol. VIII, p. 463 ff.).

Amines derivatives of the formula (7) and their salts are known in the art, commercially available or can be prepared in a known manner (see, e.g., WO 2010/051926).

The synthesis of carboxamides represented by the formula (II), preferably (II'), more preferably (IIa), can, however, also be carried out using coupling reagents such as dicyclohexylcarbodiimide and additives such as 1-hydroxybenzotriazole (König et al. Chem. Ber. (1970), 788-798). It is also possible to use coupling reagents such as 1-ethyl-3-(3-dimethylaminopropyl)carbodiimide, 1,1'-carbonyl-1H-imidazole and similar compounds.

Coupling reagents which are used for carrying out the synthesis process are all those which are suitable for the preparation of an ester or amide bond (cf. e.g. Bodansky et al., Peptide Synthesis, 2nd ed., Wiley & Sons, New York, 1976; Gross, Meienhofer, The Peptide: Analysis, Synthesis, Biology (Academic Press, New York, 1979).

Furthermore, mixed anhydrides can also be used for the synthesis of (II), preferably (II'), more preferably (IIa) (see, e.g., Anderson et al, J. Am. Chem. Soc (1967), 5012-5017). In this process it is possible to use various chloroformates, such as, for example, isobutyl chloroformate, isopropyl chloroformate. Similarly, diethylacetyl chloride, trimethylacetyl chloride and the like can be used for this.

In general, Step 6 can be carried out optionally/if appropriate, in the presence of a suitable diluent/solvent and, optionally/if appropriate, in the presence of suitable basic reaction auxiliary.

The process according to the invention can be performed in the presence of a diluent/solvent. Useful diluents for this purpose include all inert organic solvents, preferably aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, more preferably are used chlorobenzene and toluene.

Preferred diluents are aliphatic, alicyclic or aromatic hydrocarbons, for example petroleum ether, hexane, heptane, cyclohexane, methylcyclohexane, benzene, toluene, xylene or decalin; and halogenated hydrocarbons, for example chlorobenzene, dichlorobenzene, dichloromethane, chloroform, tetrachloromethane, dichloroethane or trichloroethane; e.g. toluene or chlorobenzene.

The solvent which may be used is any solvent which does not adversely affect the reaction, such as, for example, water. Of suitability are aromatic hydrocarbons such as benzene or toluene; halogenated hydrocarbons such as dichloromethane, chloroform or tetrachloromethane, open-chain or cyclic ethers such as diethyl ether, dioxane, tetrahydrofuran or 1,2-dimethoxyethane; esters such as ethyl acetate and butyl acetate; ketones such as, for example, acetone, methyl isobutyl ketone and cyclohexanone; amides such as dimethylformamide and dimethylacetamide; nitriles such as acetonitrile; and other inert solvents such as 1,3-dimethyl-2-imidazolidinone; the solvents can be used alone or in combination of two or more.

The base (basic reaction auxiliary) used can be an acid acceptor such as an organic base such as triethylamine, ethyldiisopropylamine, tri-n-butylamine, pyridine and 4-dimethylaminopyridine; furthermore, the following bases can, for example, be used: alkali metal hydroxides, such as, for example, sodium hydroxide and potassium hydroxide; carbonates such as sodium hydrogencarbonate and potassium carbonate; phosphates such as dipotassium hydrogenphosphate and disodium phosphate; alkali metal hydrides, such as sodium hydride; alkali metal alcoholates, such as sodium methanolate and sodium ethanolate. These bases can be used in ratios of from 0.01 to 5.0 mole equivalents based on (8) and (7'). Furthermore, silver(I) cyanide can also be used as base and activator (see, e.g., Journal of Organic Chemistry. 1992, 57, 4394-4400; Journal of Medicina Chemistry 1992, 35, 3905-3918; Journal of Organic Chemistry 2003, 68, 1843-1851).

However, in one preferred embodiment of the present invention, Step 6 is carried out in the absence of an acid acceptor and the leaving group is Cl or F, more preferably Cl.

In the context of the invention, "in the absence of an acid acceptor" means in the absence of an acid acceptor other than the amine reactant (8) or, in other words, "in the absence of an additional acid acceptor wherein "additional" means in addition to the amine derivative of the formula (8) (or its salts (8') which is part of the reaction. An "additional acid acceptor" in the sense of the present invention can be a base in addition to the amine compound according to the invention or compounds which reduce the strength of a formed acid such as salts, e.g. silvercyanide (AgCN), which are able to transform strong acids which are formed during the reaction (leaving group anion plus hydrogen cation) into insoluble salts and weak acids (e.g. formed HCl (if the leaving group is chlorine) reacts with AgCN to insoluble AgCl and weak base HCN).

Surprisingly, the carboxamides of the formula (II) can be prepared in the absence of an acid acceptor with good yields in high purity and selectivity. A further advantage of the process according to the invention is that the workup is simpler, since an acid acceptor is not needed. This causes fewer or no waste water, an easier purification process without prior isolation by addition of an aliphatic alcohol in the same reaction vessel, and the process can be run in a higher concentration. The resulting product has then been obtained with a surprising purity superior to 90% or even close to 100%, and with less reagent and effort, while prior conditions in presence of an acid acceptor generally leads to a purity close to less than 90% The process according to the invention becomes more economically viable.

Thus, one preferred embodiment refers to a reaction for the production of compounds of formula (IIa)

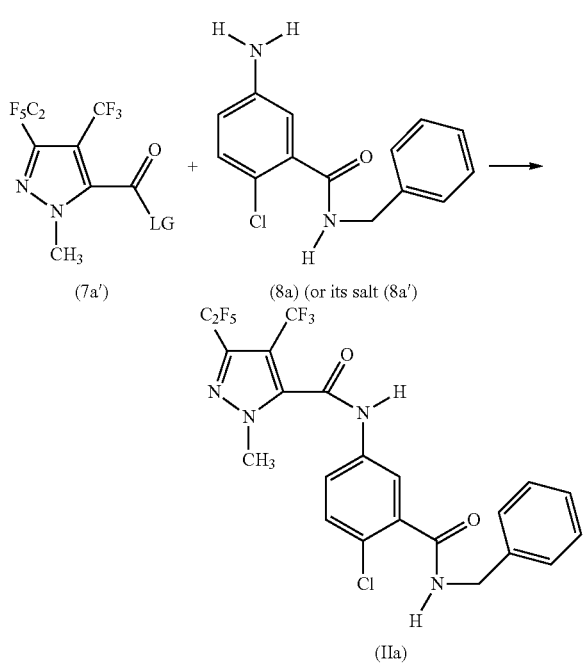

wherein leaving group LG refers to F, Cl, Br or I, preferably F or Cl, and
in the absence of an acid acceptor in addition to compound (8a).

The suitable reaction temperature is in the range from −20° C. up to the boiling point of the particular solvent. In general, the reaction temperature is between 70° C. to 150° C., preferably between 80° C. to 140° C., e.g. 100° C. or around 100° C. such as 80° C. to 130° C. or 80° C. to 120° C.

The reaction time is between 1 min and 96 h depending on the choice of volume, reactants, solvents and reaction temperature.

For the process of Step 6, generally between 0.8 and 1.5 mol, preferably 0.8 to 1.4 mol, 0.9 to 1.4 mol, equimolar amounts or 1 to 1.2 mol of amine derivative of the formula (8) or its salt, preferably (8a) or (8a'), are used per mole of the pyrazole-carboxamide derivatives (7').

One preferred embodiment refers to a reaction of a compound (8a) or its salt (8a'), respectively, with compound (7'), wherein X is Cl and wherein the ratio of compound (8a) (or its salt (8a')) and (7') wherein X is Cl is between 1:1 or 1:1.3, preferably between 1:1 to 1:2 such as between 1:1 to 1:1 or even 1:1.

Depending on the choice of volume, reactants, solvents and reaction temperature, the reaction time can vary between one minute and 96 h. Typically, the reaction time is up to 15 hours, but the reaction can also be terminated even earlier in the case of complete conversion. Preference is given to reaction times of 5-10 hours.

The reaction of Step 6 is generally performed under standard pressure. However, it is possible to work under elevated or reduced pressure—generally between 0.1 bar and 10 bar It is preferable to work under reduced pressure to remove HCl from the reaction volume.

The reaction of Step 6 can generally be performed under atmosphere. However, it is preferred to carry out the process under protective gas such as argon. or nitrogen.

Moreover the skilled person will understand that it is also possible to react a compound of formula (7') with a compound of formula (8*), wherein the —C(=O)—NH-Q moiety of compounds of formula (8) is replaced by a C(=O)—OH or C(=O)—PG moiety in a compound of formula (8*), wherein PG stands for any protective group of a carboxylic group (e.g. a methylesther, i.e. PG represents —O-methyl). The deprotection of the carboxylic moiety of the resulting compound (II*) of a reaction with a compound (8*) and/or activating of the carboxylic moiety and/or coupling with an amine to arrive at a compound of formula (II) are well known to a skilled person. Compounds of the general structure (II*) can be synthesized by reacting an amine of the general structure (7) with activated carboxylic acid derivatives of the general structure (8*). In this connection, the same conditions apply for the choice of solvent, the reaction conditions, the reaction time and the reagents as for the synthesis of (II), described above.

Step 5

Compounds of the general structure (8) can be synthesized by reacting an amine of the general structure (10) with activated carboxylic acid derivatives of the general structure (9). In this connection, the same conditions apply for the choice of solvent, the reaction conditions, the reaction time and the reagents as for the synthesis of (II), preferably (II'), more preferably (IIa), described in Step 6 above.

Compounds of Formula (III)

The present invention also refers to a process to produce an insecticidal compound of formula (III) or (III') based on the preparation of compounds of formula (I).

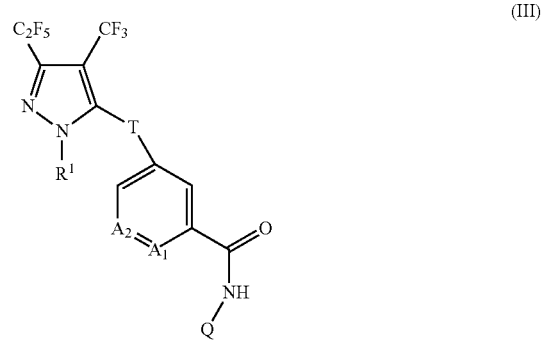

in which
$R^1$ is $(C_1-C_4)$-alkyl, preferably methyl; and
$A_1$ is C—$R^2$;
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH-cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and A$_2$ is C—R$^3$ or nitrogen;

R$^3$ is hydrogen, methyl, fluorine or chlorine, preferably hydrogen; and

Q is hydrogen, cyano, hydroxy, formyl or one of the groupings C$_1$-C$_6$-alkyl, C$_3$-C$_6$-alkenyl, C$_3$-C$_6$-alkynyl, C$_3$-C$_9$-cycloalkyl, C$_3$-C$_9$-heterocycloalkyl, C$_1$-C$_4$-alkoxy, C$_4$-C$_{15}$-alkylcycloalkyl, C$_4$-C$_{15}$-cycloalkylalkyl, C$_1$-C$_6$-hydroxyalkyl, C$_6$-aryl-C$_1$-C$_3$-alkyl, C$_5$-C$_6$-heteroaryl-C$_1$-C$_3$-alkyl, C$_1$-C$_4$-aminoalkyl, aminocarbonyl-C$_1$-C$_4$-alkyl or C$_1$-C$_4$-alkyl-amino-C$_1$-C$_4$-alkyl which are optionally substituted with one, two, three, four or five, preferably with one or two, more preferably with one, substituents independently selected from the group consisting of hydroxy, nitro, amino, halogen, C$_1$-C$_3$-alkoxy, cyano, hydroxycarbonyl, C$_1$-C$_4$-alkoxycarbonyl, C$_1$-C$_4$-alkylcarbamoyl, C$_4$-C$_6$-cycloalkylcarbamoyl and optionally independently with one, two or three substituents selected from the group consisting of halogen, cyano, nitro, hydroxycarbonyl, C$_1$-C$_2$-alkylcarbamoyl, C$_1$-C$_2$-alkyl, halogenated C$_1$-C$_2$-alkyl and C$_1$-C$_2$-alkoxy substituted phenyl; preferably Q is C$_3$-C$_6$-cycloalkyl, or C$_3$-C$_6$-cycloalkyl which is substituted with at least one substituent selected from the group consisting of chlorine, fluorine, bromine, iodine, cyano and hydroxy, or C$_6$-aryl-C$_1$-C$_3$-alkyl; more preferably cyclopropyl, 1-cyano-cyclopropyl or benzyl (—CH$_2$—C$_6$H$_5$);

T represents one of the 5-membered heteroaromatics T1-T8 listed below, where the bond to the pyrazole head group is marked with an asterisk *,

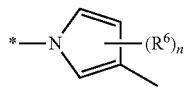
T1

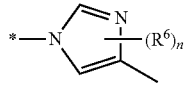
T2

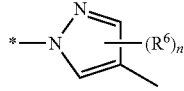
T3

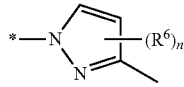
T4

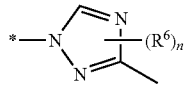
T5

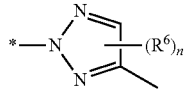
T6

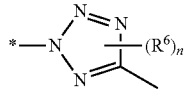
T7

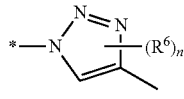
T8 wherein

R$^6$ independently of one another represents halogen, cyano, nitro, amino or optionally substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, and n represents the values 0-2, preferably 0, provided that n is 0 or 1 in T5, T6 and T8 and provided n is 0 in T7;

preferably, a compound of formula (III) is a compound of formula (III')

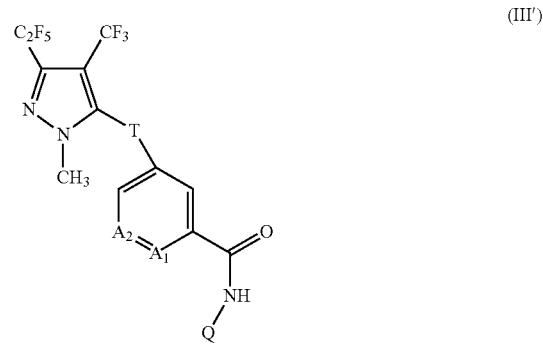

(III')

wherein A$_1$ and A$_2$ and T and Q have the meanings described above for a compound of formula (III) characterized in that the process comprises steps 1 and 2 as described above.

For clarity sake, if n in any formula described herein is 0 (zero), carbon ring atoms with a free valence are then substituted by hydrogen.

In one preferred embodiment, the compound of formula (III) is compound (IIIa) defined by the following substituents:

| R$^1$ | T | n | R$^6$ | A$^1$ | A$^2$ | Q |
|---|---|---|---|---|---|---|
| CH$_3$ | T3 | 0 | — | C—Cl | C—H | 1-cyanocyclopropyl ![structure] |

The new and inventive process for preparing a compound of formula (III), preferably (III'), more preferably (IIIa), is characterized in that the process steps 1 and 2 as described above. In a further preferred embodiment, the process comprises in addition to steps 1 and 2 as described above the subsequent Step 7 and Step 8:

Step 7

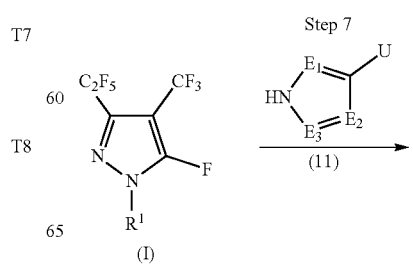

17
-continued

Step 8

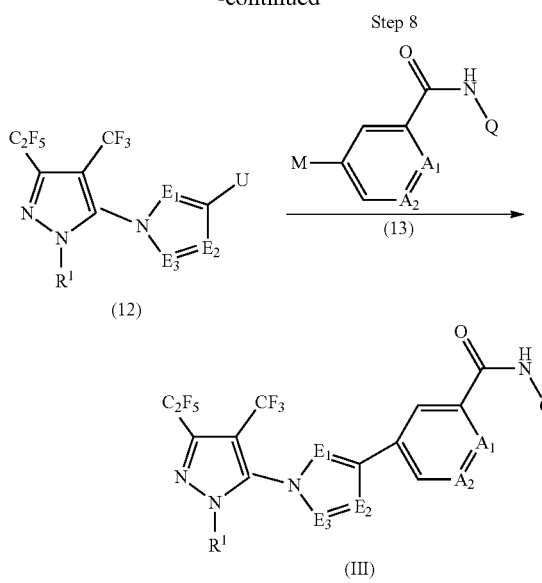

(12)

(III)

The radicals $A_1$, $A_2$, $R^1$ and Q have the meanings described for compound (III). Preferably, $R^1$ is methyl. The five-membered cycles of $E_1$-$E_3$, carbon and nitrogen represent the 5-membered heterocycles defined under T. U represents bromine, iodine or triflate if M represents a boronic acid, boronic ester or trifluoroboronate. U represents a boronic acid, boronic ester or trifluoroboronate if M represents bromine, iodine or triflate.

Step 7

The compounds of the general structure (12) can be prepared by processes known from the literature by, e.g., nucleophilic substitution of F at the aromatic ring (WO2007-107470; Sakya et al., Tetrahedron Letters 2003, 44, 7629-7632) from the appropriate starting materials of formula (I), preferably (Ia), more preferably (Ib), and (11).

Step 8

Compounds of formula (III) or (III'), preferably compound (IIIa), can be prepared by using palladium-catalysed reactions with the reaction partners (12) and (13) (see, e.g., WO 2005/040110 or WO 2009/089508). The compounds of the general structure (13) are either commercially available or can be prepared by processes known to the person skilled in the art.

Moreover, the skilled person is aware that it is alternatively possible to react a compound of formula (12) with a compound of formula (13*), wherein the —C(=O)—NH-Q moiety of compounds of formula (13) is replaced by a C(=O)—OH or C(=O)—PG moiety in a compound of formula (13*), wherein PG stands for any protective group of a carboxylic group (e.g. an alkylester such as methylester, i.e. PG represents —O-methyl). The deprotection of the carboxylic moiety of the resulting compound (III*) of a reaction with a compound (13*) and/or activating of the carboxylic moiety and/coupling with an amine to arrive at a compound of formula (III) are well known to a skilled person.

In sum, compounds of the general structure (III) can be synthesized by reacting an amine of the general structure (10) with activated carboxylic acid derivatives of the general structure (III*). In this connection, the same conditions apply for the choice of solvent, the reaction conditions, the reaction time and the reagents as for the synthesis of (II), described in Step 6 above.

18

Compounds of Formula (III")

In another preferred embodiment, the invention refers to a process to prepare a compound of formula (III"), preferably of formula (III'''), e.g., known from WO 2012/107434:

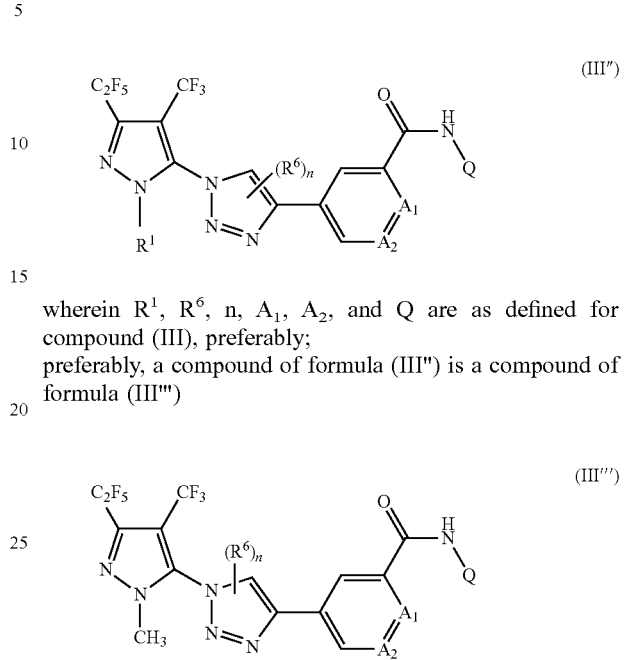

wherein $R^1$, $R^6$, n, $A_1$, $A_2$, and Q are as defined for compound (III), preferably;
preferably, a compound of formula (III") is a compound of formula (III''')

wherein $R^6$, n, $A_1$, $A_2$ and Q are as defined for a compound of formula (III), preferably, wherein n is 0 characterized in that the process comprises steps 1 and 2 as described above.

In one preferred embodiment, the compound of formula (III''') is compound (IIIb) defined by the following substituents:

| n | $R^6$ | $A^1$ | $A^2$ | Q |
|---|---|---|---|---|
| 0 | — | C—Cl | C—H | 1-cyanocyclopropyl |

The process for preparing a compound of formula (III"), preferably (III'''), more preferably (IIIb), is characterized in that the process comprises steps 1 and 2 as described above. In a further preferred embodiment, the process comprises in addition to steps 1 and 2 as described above optionally Step 3 and Step 4 as described above optionally the subsequent Step 7 and Step 8 as described above or optionally the subsequent Step 9 and Step 10. Steps 11 and 12 are known in the art (see, e.g., WO 2012/107434).

Step 9

In a Step 9, a compound of formula (I), preferably of formula (Ia), can be transformed into its azido analogue of formula (14) or (14a), respectively:

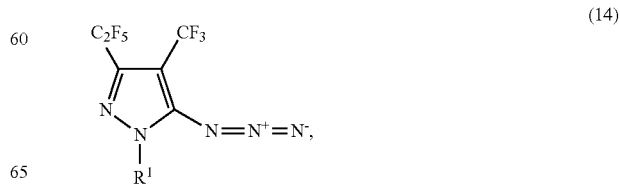

(14)

wherein $R^1$ is hydrogen, optionally halogenated $C_1$-$C_4$-alkyl or optionally halogenated cyclopropyl, preferably methyl, preferably, a compound of formula (14) is compound (14a)

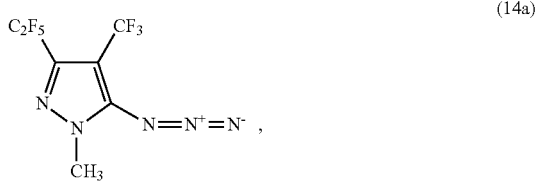

by reacting compound (I), preferably compound (Ia), more preferably compound (Ib), with an azide-donor such an alkaline metal azide (e.g., NaN$_3$).

Preferably, the reaction is carried out in a polar aprotic solvent such as tetrahydrofuran (THF), ethyl acetate (EtOAc), acetone, dimethylformamide (DMF), acetobitrile or dimethyl sulfoxide (DMSO). One preferred solvent is DMSO.

Typically, the reaction temperature is between 0° C. and 60° C., preferably between 10° C. and 30° C., more preferably between 20° C. and 30° C.

The reaction time can inter alia depend on the reaction volume and is usually between 0.5 h to 30 h.

Step 10

In a Step 10, an intermediate of formula (14), preferably of formula (14a), is reacted with an intermediate of formula (15) to give an intermediate of formula (III'"*) or preferably a compound of formula (III'"*) wherein $R^1$ is methyl, respectively:

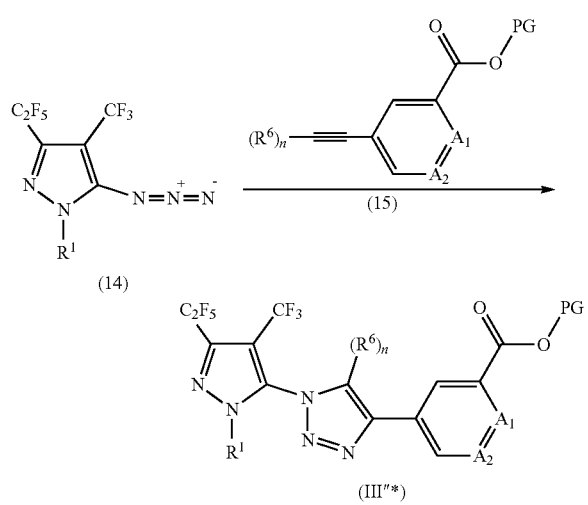

wherein $R^1$, $R^6$, $A_1$, and $A_2$ are as defined for compound (III), n is 0 or 1 and PG is any protective group of the carboxylic group such as $C_1$-$C_6$-alkyl (e.g., methyl). Preferably, $R^1$ in a compound of formula (III"*) is methyl (compound of formula (III'"*)). More preferably, $R^1$ in formula (III"*) is methyl and n in formula (III"*) is 0.

Compounds of formula (15) are commercially available or can be prepared according to methods known in the art.

Typically, the solvent for reaction of Step 10 is a polar protic solvent such as water, formic, n-butanol, isopropanol, nitromethane, ethanol, methanol, acetic acid or combinations thereof. Preferably, the solvent is n-butanol, isopropanol, ethanol, water or combinations thereof.

The reaction is carried out in the presence of copper or a copper catalyst such as copper sulfate or copper (I) iodide, optionally in the presence of a base such as N-ethyldiisopropylamine. However, also other organic bases are suitable. In case of a Cu(II) catalyst, a reducing agent such as sodium ascorbate may be used. In case of Cu(0) catalyst, such as an amine salt, an oxidizing agent may be used (see, e.g., Angewandte Chemie, International Edition (2009), 48(27), 4900-4908 and cited references, Lutz., Angew. Chem. Int. Ed. 2008, 47, 2182-2184 and cited references, and Bock et al., Eur. J. Org. Chem. (2006), 51-68 and cited references).

Starting from a compound of formula (III"*), compounds of formula (III), (III'), (III"), (III'"), (IIIb), (III""), (IV) or (IV') can be easily prepared according to methods known in the art (see, e.g. WO 2012/107434).

Step 11

Compound of formula (III"") may be prepared by reaction of a compound of formula (III"*) wherein O-PG is $C_1$-$C_6$-alkoxy via hydrolysis. For instance, in the case wherein —O-PG is methoxy or ethoxy, the hydrolysis can be done with water and a base, such as potassium hydroxide or lithium hydroxide, in the absence or in the presence of a solvent, such as, for instance, tetrahydrofurane or methanol. In the case where R is, for example, tert-butoxy, the hydrolysis is done in the presence of acid, such as trifluoroacetic acid or hydrochloric acid. The reaction is carried out at a temperature of from −120° C. to 130° C., preferably from −100° C. to 100° C.

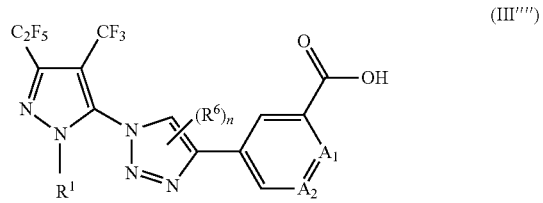

wherein $R^1$, $R^6$, n, $A_1$, and $A_2$ are as defined for compound (III), preferably $R^1$ is methyl and n is 0.

Compounds of the general structure (III) can be synthesized by reacting an amine of the general structure (10) with activated carboxylic acid derivatives of the general structure (III""). In this connection, the same conditions apply for the choice of solvent, the reaction conditions, the reaction time and the reagents as for the synthesis of (II) described in Step 6 above.

Compounds of Formula (IV)

One aspect of the present invention refers to a process for the preparation of a compound of formula (IV), preferably of formula (IV'):

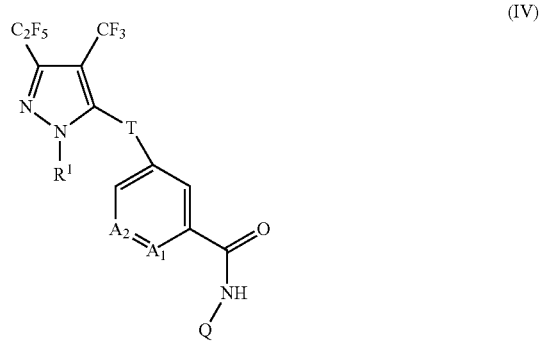

in which
R¹ is $C_1$-$C_4$-alkyl, preferably methyl; and
$A_1$ is C—R²; and
R² is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH-cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
$A_2$ is C—R³ or nitrogen; and
R³ is hydrogen, methyl, fluorine or chlorine, preferably hydrogen; and
T represents one of the 5-membered heteroaromatics T1-T9 listed below, where the bond to the pyrazole head group is marked with an asterisk *,

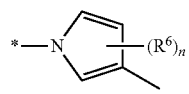
T1

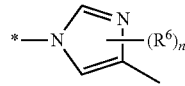
T2

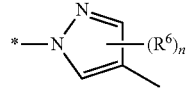
T3

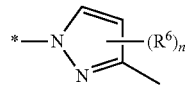
T4

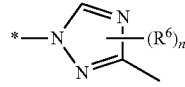
T5

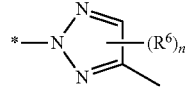
T6

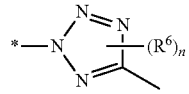
T7

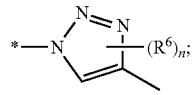
T8

*—C(=O)—NH—;
T9 and
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7.
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—$CH_2$—$C_6H_5$);
preferably, a compound of formula (IV) is a compound of formula (IV'):

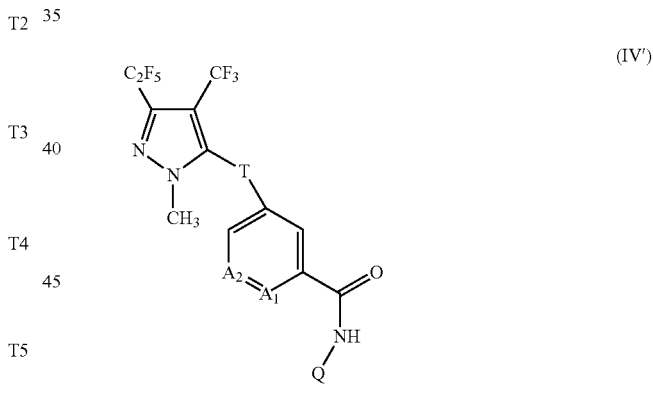

(IV')

wherein T, $A_1$, $A_2$ and Q are as defined for a compound of formula (IV), preferably wherein T is selected from T3, T8 or T9 wherein the process is characterized in that the process comprises steps 1 and 2 as described above.

One preferred embodiment refers to a process for the preparation of compound (IV) where R¹—in all formulae disclosed herein wherein R¹ is present—represents methyl.

Another preferred embodiment refers to a process for the preparation of compound (IV) where n—in all formulae disclosed herein wherein n is present—represents 0.

Another preferred embodiment refers to a process for the preparation of compound (IV) where $A_1$—in all formulae disclosed herein wherein $A_1$ is present—represents C—R², wherein R² represents hydrogen, fluorine, chlorine or bromine, most preferably wherein R² represents chlorine.

Another preferred embodiment refers to a process for the preparation of compound (IV) where $A_2$—in all formulae disclosed herein wherein $A_2$ is present—represents $C—R^3$ wherein $R^3$ represents hydrogen.

Another preferred embodiment refers to a process for the preparation of compound (IV) where T—in formula (IV) and all further formulae disclosed herein wherein T is present—represents T3, T8 or T9.

Another preferred embodiment refers to a process for the preparation of compound IV where Q—in all formulae disclosed herein wherein Q is present—represents optionally with cyano substituted $C_3$-$C_6$-cycloalkyl or $C_6$-aryl-$C_1$-C3-alkyl even more preferred Q represents optionally with cyano substituted $C_3$-cycloalkyl or benzyl, even more preferred, Q represents with cyano substituted cyclopropyl (e.g., 1-cyano-cyclopropyl) or benzyl.

Another preferred embodiment refers to a process for the preparation of compound (IV) where $R^1$—in all formulae disclosed herein wherein $R^1$ is present—represents methyl and n—in all formulae disclosed herein wherein n is present—represents 0 and $A_1$—in all formulae disclosed herein wherein $A_1$ is present—represents C—Cl and $A_2$—in all formulae disclosed herein wherein $A_2$ is present—represents C—H and where T—in formula (IV) and all further formulae disclosed herein wherein T is present—represents T3, T8 or T9, and Q in all formulae disclosed herein wherein Q is present represents optionally with cyano substituted $C_3$-$C_6$-cycloalkyl or $C_6$-aryl-$C_1$-$C_3$-alkyl.

Another preferred embodiment refers to a process for the preparation of compound IV where $R^1$—in all formulae disclosed herein wherein $R^1$ is present—represents methyl and T—in all formulae disclosed herein wherein T is present—represents T3, T8 or T9 and n—in all formulae disclosed herein wherein n is present—represents 0 and $A_1$—in all formulae disclosed herein wherein $A_1$ is present—represents C—Cl and $A_2$—in all formulae disclosed herein wherein $A_2$ is present—represents C—H and Q—in all formulae disclosed herein wherein Q is present—represents with cyano substituted cyclopropyl (e.g. 1-cyano-cyclopropyl) or benzyl.

The present invention also refers to a process for the preparation of a compound of formula (6), preferably of formula (6a), comprising the steps 1 and 2 as described above optionally Step 3 and Step 4 as described above.

The present invention also refers to a process for the preparation of a compound of formula (6), preferably of formula (6a), comprising the steps 1 and 2 as described above optionally Step 3 and Step 4 as described above. Or comprising the steps 1 and 2 as described above.

The present invention also refers to a process for the preparation of a compound of formula (7), preferably of formula (7a), comprising the steps 1 and 2 as described above.

The present invention also refers to a process for the preparation of a compound of formula (7), preferably of formula (7a), comprising the steps 1 and 2 as described above; or to a process for the preparation of a compound of formula (I), preferably of formula (7a) comprising the steps 1 and 2 as described above and Step 3 and Step 4 as described above.

In one aspect, the present invention also refers to the use of compounds of formula (I) prepared by a process comprising at least steps 1 and 2 as described above to prepare a compound of formula (II), preferably of formula (IIa).

Moreover, the present invention also refers to the use of compounds of formula (1) prepared by a process comprising at least steps 1 and 2 as described above to prepare a compound of formula (III), preferably of formula (III'), more preferably of formula (IIIa).

Moreover, the present invention also refers to the use of compounds of formula (1) prepared by a process comprising at least steps 1 and 2 as described above to prepare a compound of formula (III''), preferably of formula (III'''), more preferably of formula (IIIb).

Moreover, the present invention also refers to the use of compounds of formula (1) prepared by a process comprising at least steps 1 and 2 as described above to prepare a compound of formula (IV), preferably of formula (IV').

SUMMARY

One aspect of the present invention refers to a process for the synthesis of 5-fluoro-1H-pyrazoles of the general formula (I)

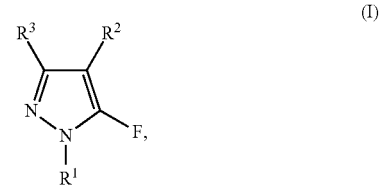

wherein an olefin of the general formula (a)

in a first step
a) is reacted with water and a base, and in a second step
b) is reacted with a hydrazine of the formula (b)

wherein
$R^1$ is selected from $C_1$-$C_6$ alkyl, $C_5$-$C_{10}$ aryl, preferably $C_1$-$C_6$ alkyl, more preferably methyl;
$R^2$ is a trihalomethyl moiety with at least one fluorine atom; and
$R^3$ is selected from $C_1$-$C_5$ haloalkyl.
One preferred embodiment refers to a process, wherein
$R^1$ is methyl
$R^2$ is $CF_3$
$R^3$ is $C_2F_5$,
One preferred embodiment refers to a process, wherein the base is triethylamine.

Another aspect refers to a process for the synthesis of 5-fluoro-1H-pyrazoles of the general formula (I),

wherein a compound of formula (c)

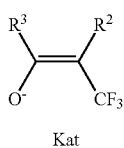

is reacted with a hydrazine of formula (b)

wherein
$R^1$ is selected from $C_1$-$C_6$ alkyl, $C_5$-$C_{10}$ aryl;
$R^2$ is a trihalomethyl moiety with at least one fluorine atom; and
$R^3$ is selected from $C_1$-$C_5$ haloalkyl,
and wherein Kat is any organic or inorganic kation except from a proton.

One preferred embodiment refers to a process, wherein
$R^2$ is trifluoromethyl,
$R^3$ pentafluoromethyl,
and wherein Kat is $(HNAlkyl_3)^+$.

Yet another aspect refers to a process for the preparation of a compound of formula (IV)

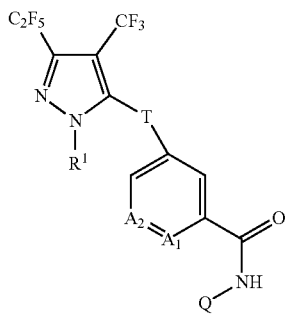

in which
$R^1$ is $C_1$-$C_4$-alkyl; and
$A_1$ is C—$R^2$; and
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH-cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
$A_2$ is C—$R^3$ or nitrogen; and
$R^3$ is hydrogen, methyl, fluorine or chlorine, preferably hydrogen; and T represents one of the groups $T_1$-$T_9$ listed below, where the bond to the pyrazole head group is marked with an asterisk *,

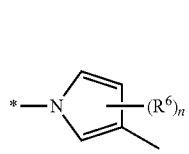 T1

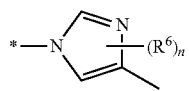 T2

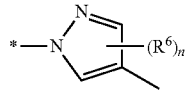 T3

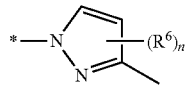 T4

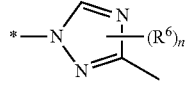 T5

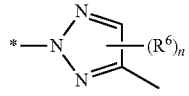 T6

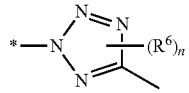 T7

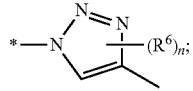 T8

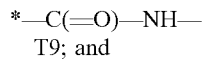

or
*—C(=O)—NH—
T9; and
$R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7; and
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—$CH_2$—$C_6H_5$);

comprising the steps according to any one of the above paragraphs.

One preferred embodiment refers to a process, wherein a compound of formula (IV) is a compound of formula (II), preferably of formula (II').

One preferred embodiment refers to a process wherein a compound of formula (IV) is compound (IIa).

One preferred embodiment refers to a process, further comprising the steps of:

reacting compound (I) with a cyano-donor to prepare intermediate of formula (6)

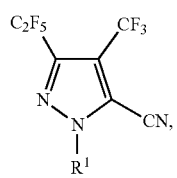

(6)

wherein $R^1$ is ($C_1$-$C_4$)-alkyl; and reacting compound (6) with an inorganic strong base in a first hydrolysis step followed by adding an inorganic acid in a second hydrolysis step to prepare intermediate of formula (7)

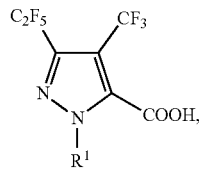

(7)

wherein
$R^1$ is ($C_1$-$C_4$)-alkyl; and reacting a compound of formula (8) or its salt (8') with an activated form (7') of compound (7)

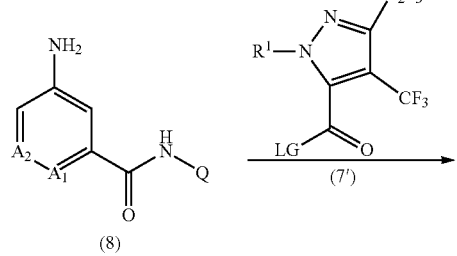

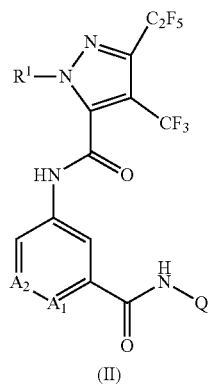

(II)

wherein $R^1$, $A_1$, $A_2$, and Q are as defined in claim 5 and LG is any leaving group, to prepare a compound of formula (II).

One preferred embodiment refers to a process, wherein a compound of formula (IV) is a compound of formula (III)

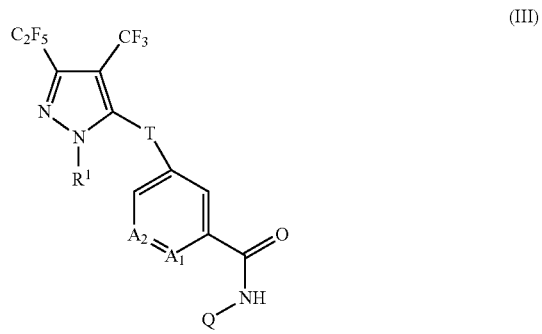

(III)

in which
$R^1$ is ($C_1$-$C_4$)-alkyl; and
$A_1$ is C—$R^2$;
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH— cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
$A_2$ is C—$R^3$ or nitrogen;
$R^3$ is hydrogen, methyl, fluorine or chlorine, preferably hydrogen; and
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$- alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—$CH_2$—$C_6H_5$);

T represents one of the 5-membered heteroaromatics T1-T8 listed below, where the bond to the pyrazole head group is marked with an asterisk *,

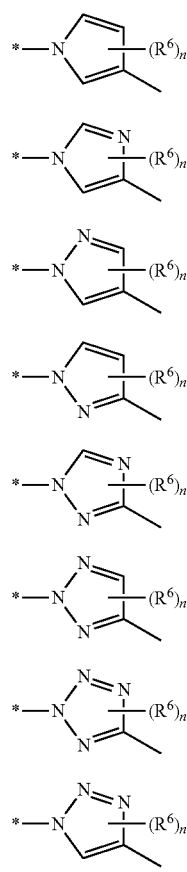

wherein
$R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7.

One preferred embodiment refers to a process, wherein a compound of formula (III) is compound of formula (III'), more preferably compound (IIIa) or compound (IIIb).

One preferred embodiment refers to a process, further comprising the steps of
reacting a compound of formula (I) with an intermediate of formula (11) by nucleophilic substitution of the fluoride at the ring position of a compound of formula (I) (herein referred to as Step 9)

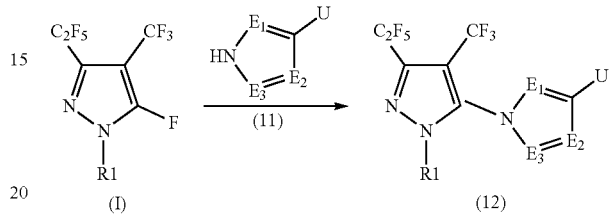

wherein
$R^1$ is optionally halogenated ($C_1$-$C_4$)-alkyl or optionally halogenated cyclopropyl; and
U represents bromine, iodine, triflate, boronic acid, boronic ester or trifluoroboronate; and
the five-membered cycles of $E_1$-$E_3$, carbon and nitrogen represent the 5-membered heterocycles selected from the group consisting of

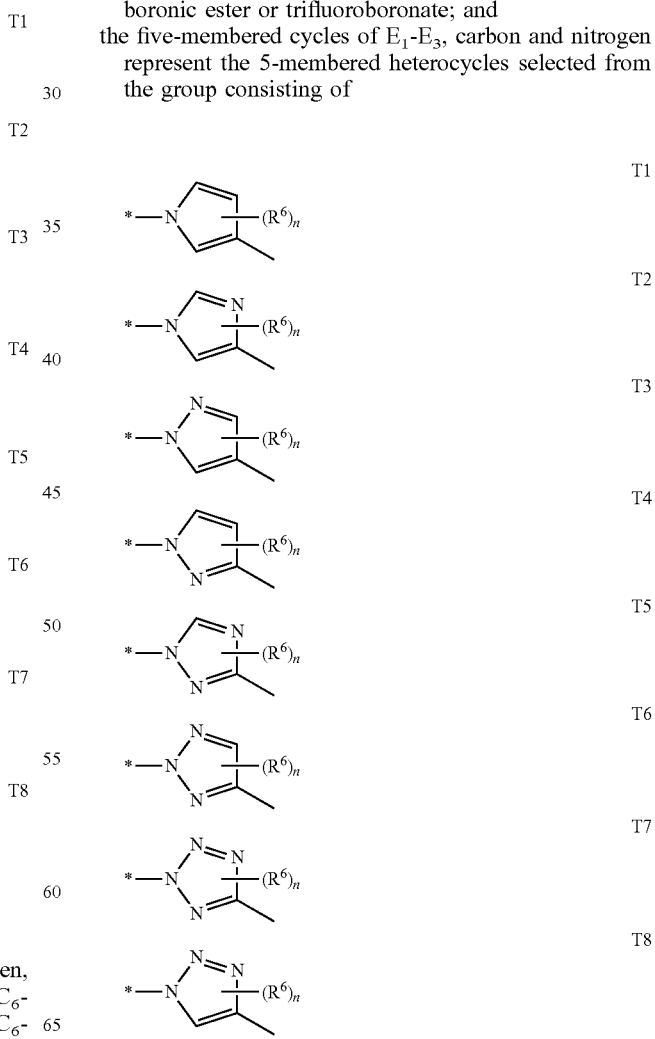

wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7;

to prepare an intermediate of formula (12); and reacting a compound of formula (12) and a compound of formula (13) (herein referred to as Step 10)

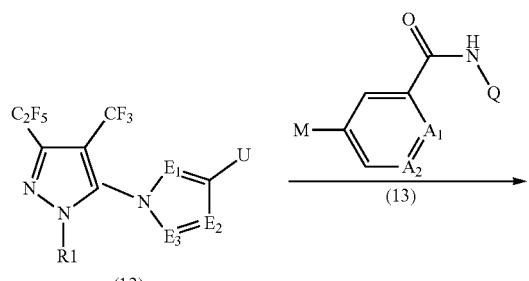

(12)

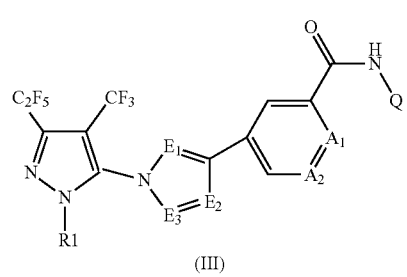

(III)

wherein $R^1$, $A_1$, $A_2$, and Q are as defined for a compound of formula (III) and U represents bromine, iodine, triflate, boronic acid, boronic ester or trifluoroboronate; and the five-membered cycles of $E_1$-$E_3$, carbon and nitrogen represent the 5-membered heterocycles selected from the group consisting of

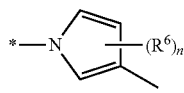

T1

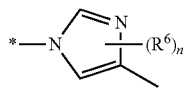

T2

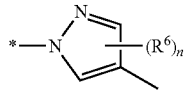

T3

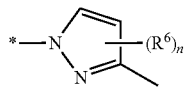

T4

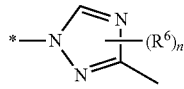

T5

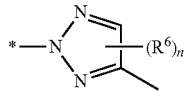

T6

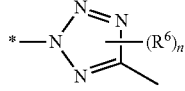

T7

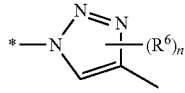

T8 wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7; and M represents bromine, iodine or triflate when U represents a boronic acid, boronic ester or trifluoroboronate; or M represents a boronic acid, boronic ester or trifluoroboronate when U represents bromine, iodine or triflate to prepare a compound of formula (III).

One preferred embodiment refers to a process, wherein a compound of formula (IV) is a compound of formula (III″), preferably of formula (III‴).

One preferred embodiment refers to a process
a) further comprising the steps as described in claim 11; or
b) further comprising the steps of
reacting a compound of formula (I) and an azide-donoer to prepare intermediate (14)

(14)

C₂F₅, CF₃ structure with N=N⁺=N⁻ wherein $R^1$ is as defined for a compound of formula (III); and reacting intermediate (14) with an intermediate of formula (15) to give an intermediate (III‴*) (herein referred to as Step 12)

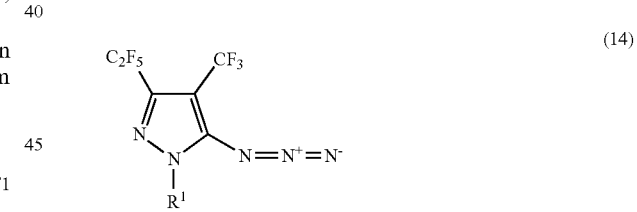

(14)

-continued

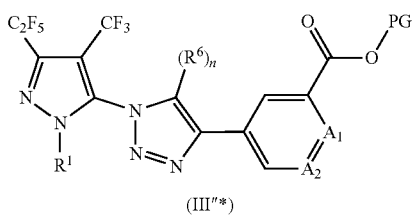

(III″*)

wherein $R^1$, $R^6$, $A_1$, and $A_2$ are as defined for compound (III), n is 0 or 1 and PG is any protective group of the carboxylic group such as $C_1$-$C_6$-alkyl (e.g., methyl).

One preferred embodiment refers to a process, wherein $R^1$ is methyl.

The invention is illustrated by the non-limiting examples below.

EXAMPLE 1 N-methyl-3-pentafluoroethyl-4-trifluoromethyl-5-fluoro-1H-pyrazole In a 3-neck flask equipped with condenser, thermometer, and a dropping funnel 130 ml methylene chloride and perfluoro-2-methyl-2-pentene (19.6 g, 0.065 mol) was placed and then 1.2 g water were added. The mixture was cooled to 0° C. and $Et_3N$ (16.4 g, 0.16 mol) was added at a temperature ranging from 0° C. to 5° C. The mixture was stirred at this temperature for 15-30 min and 40% solution of methylhydrazine in water (8 g) was slowly added to this mixture at 0° C. The reaction mixture was stirred for 1 h at 5° C. and finally for 8 h at 20° C. The mixture was washed with water (3×50 ml), the organic layer was dried over $Na_2SO_4$ and the solvent was distilled off under atmospheric pressure. The crude product was purified via vacuum distillation. The yield of N-methyl-3-pentafluoroethyl-4-trifluoromethyl-5-fluoro-1H-pyrazole was 14.8 g. (80%), boiling point 62-65° C. at 17 mbar.

$^{19}F$ NMR δ: 53.7 (3F), 83.9 (3F), 112.1 (2F), 125.1 (1F) ppm.

EXAMPLE 2 N-methyl-3-pentafluoroethyl-4-trifluoromethyl-5-fluoro-1H-pyrazole In a 3-neck flask equipped with condenser, thermometer, and a dropping funnel 100 ml methylene chloride and (perfluoro-2-methyl-2-penten-)3-triethylammonium-enolate (25.9 g, 0.065 mol) was placed, and then a 40% solution of N-methylhydrazine in water (8 g) was slowly added to this mixture at 0° C. The reaction mixture was stirred for 1 h at 5° C., and finally for 2 h at 20° C. The mixture was washed with water (3×50 ml), the organic layer was dried over $Na_2SO_4$ and the solvent was distilled off under atmospheric pressure. The crude product was purified via vacuum distillation. The yield of N-methyl-3-pentafluoroethyl-4-trifluoromethyl-5-fluoro-1H-pyrazole was 15, 8 g. (85%), boiling point 62-65° C. at 17 mbar.

$^{19}F$ NMR δ: 53.7 (3F), 83.9 (3F), 112.1 (2F), 125.1 (1F) ppm.

EXAMPLE 3 (Step 3)

Preparation of 5-Cyano-1-methyl-3-pentafluoroethyl-4-trifluoromethyl-1H-pyrazole (Intermediate (6a))

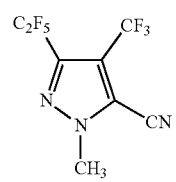

(6a)

28.6 g (0.1 mol) of 5-fluoro-1-methyl-3-pentafluoroethyl-4-trifluoromethylpyrazole (compound (Ia)) and 9.7 g (0.15 mol) of potassium cyanide are suspended in 150 ml of acetonitrile and then heated under reflux for 5 h under a protective gas atmosphere. After cooling, the precipitate (KCN, KF) was filtered off, and the solvent was removed in vacuo 300 mbar to give a brawn oil (27.8 g, 95%) which was used for further step without any purification.

$^1$H-NMR (400 MHz, $d_3$-acetonitrile): δ=4.11 (s, 3H, $CH_3$) ppm
$^{19}$F-NMR (400 MHz, $CDCl_3$): δ=−56.7 (3F), −111.4 (3F), −111.6 (2F) ppm.
GC-MS: Retention time 2.67 min; mass (m/z): 224 (M)$^+$.

EXAMPLE 4 (Step 4)

Preparation of 1-Methyl-3-pentafluoroethyl-4-trifluoromethyl-1H-pyrazole-5-carboxylic acid (Intermediate (7a))

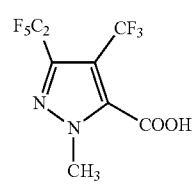

(7a)

29.3 g (0.1 M) of 5-cyano-1-methyl-3-pentafluoroethyl-4-trifluoromethylpyrazole (compound (6a)) and 110 g of 10% NaOH were heated in an oil bath at 100° C. for 6 h until clear solution formed. After cooling to 5° C., the reaction mixture was slowly acidify to pH 1 by adding of 37% HCl to give a white crystals which were filtered off, washed with 40 ml cold water and dried yielding 28 g (7a) of 1-methyl-3-pentafluoroethyl-4-trifluoromethylpyrazole-5-carboxylic acid) as a white solid with m.p. 120-122° C.

$^1$H-NMR (400 MHz, $d_3$-acetonitrile) δ=4.08 (s, 3H, $CH_3$) ppm;
HPLC-MS$^{a)}$: log P=1.86; mass (m/z): 313.0 (M+H)$^+$.

EXAMPLE 5 (Step 7)

Preparation of 4-bromo-2'-methyl-5'-(pentafluoroethyl)-4'-(trifluoromethyl)-2'H-1,3'-bipyrazole (Intermediate (12))

2.00 g (6.99 mmol) of 5-fluoro-1-methyl-3-(pentafluoroethyl)-4-(trifluoromethyl)-1H-pyrazole (compound (Ia)), 1.03 g (6.99 mmol) of 4-bromo-1H-pyrazole (compound of formula (11)) and 1.93 g of potassium carbonate are suspended in 50 ml of tetrahydrofuran p.a. The reaction mixture is heated under reflux for 16 h. The cooled reaction mixture is filtered and the solvent is removed under reduced pressure. The residue is purified by column chromatography on silica gel.

This gives 0.69 g of 4-bromo-2'-methyl-5'-(pentafluoroethyl)-4'-(trifluoromethyl)-2'H-1,3'-bipyrazole as a colourless solid.

$^1$H-NMR (400 MHz, $d_3$-acetonitrile): δ=8.00 (s, 1H), 7.91 (s, 1H), 3.71 (s, 3H).

HPLC-MS$^{a)}$: log P=4.14, mass (m/z)=413 [M+H]$^+$.

EXAMPLE 6 (Step 8)

Preparation of 2-Chloro-N-1-cyano-cyclopropyl-5-[2'-methyl-5'-(pentafluoroethyl)-4'-(trifluoromethyl)-2'H-1,3'-bipyrazol-4-yl]benzamide (Compound (IIIa))

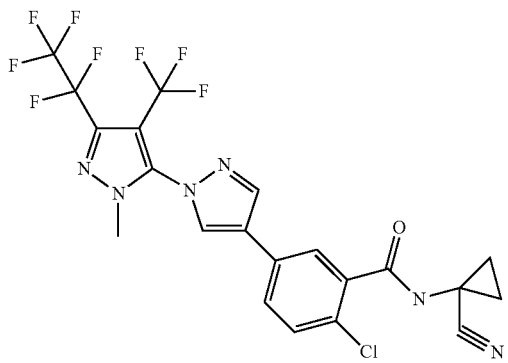

150 mg (0.36 mmol) 4-bromo-2'-methyl-5'-(pentafluoroethyl)-4'-(trifluoromethyl)-2'H-1,3'-bipyrazole, 126 mg (0.36 mmol) 2-chloro-N-(1-cyanocyclopropyl)-5-(4,4,5,5-tetramethyl-1,3,2-dioxaborolane-2-yl)benzamide, 21 mg (0.01 mmol) tetrakis(triphenylphosphin)palladium and 1.1 ml of 1M aqueous sodium bicarbonate were mixed with 10.5 ml isopropanol and heated under reflux for 3 h. The solvent is removed under reduced pressure and the residue is dissolved in ethylacetat. The organic phase was washed two times with water, dried over Na$_2$SO$_4$, and filtered. The solvent is removed under reduced pressure. The residue was purified vie column chromatography with silica gel, yielding 98 mg 2-chloro-N-(1-cyanocyclopropyl)-5-[2'-methyl-5'-(pentafluoroethyl)-4'-(trifluoromethyl)-2'H-1,3'-bipyrazole-4-yl]benzamide as colorless solid.

$^1$H-NMR (400 MHz, $d_3$-Acetonitril): δ=$^1$H-NMR (400 MHz, d3-Acetonitril): δ=8.27 (s, 1H), 8.25 (s, 1H), 7.75 (d, 1H), 7.70 (dd, 1H), 7.62 (s, 1H), 7.51 (d, 1H), 3.75 (s, 3H), 1.56-1.60 (m, 2H), 1.33-1.36 (m, 2H).

HPLC-MS$^{a)}$: log P=3.72, Masse (m/z)=553.1 [M+H]$^+$.

EXAMPLE 7 (Step 9)

Preparation of 5-Azido-1-methyl-3-pentafluoroethyl-4-trifluoromethyl-1H-pyrazole (Intermediate (14), R$^1$=methyl)

5-Fluoro-1-methyl-3-pentafluoroethyl-4-trifluoromethyl-1H-pyrazole (prepared according to steps 1 to 4; 7 mmol) is added to a mixture of dimethyl sulfoxide (DMSO) (10 ml). Sodium azide (0.5 g; 7.7 mmol) is then added into the mixture, which is kept at room temperature. The mixture is stirred overnight at RT. After the reaction is complete, a mixture of water (100 mL) and diethyl ether (100 mL) is added. The phases are separated and the aqueous phase extracted twice with diethyl ether. This compound is used without extra purification.

EXAMPLE 8 (Step 10)

Preparation of 2-Chloro-5-[1-(2-methyl-5-pentafluoroethyl-4-trifluoromethyl-2H-pyrazol-3-yl)-1H-[1,2,3]triazol-4-yl]-benzoic acid methyl ester (see Intermediate (III"*))

2-Chloro-5-ethynyl-benzoic acid methyl ester (1.13 g, 5.8 mmol) and 5-Azido-1-methyl-3-pentafluoroethyl-4-trifluoromethyl-1H-pyrazole (1.80 g, 5.8 mmol) is suspended in a mixture of water and t-BuOH (30 ml). Sodium ascorbate (0.600 ml 1 M sol. in water, freshly prepared) is added to the mixture followed by copper (II) sulfate pentahydrate (0.015 g). The resulting heterogeneous mixture is stirred vigorously for 96 hours. The reaction mixture is diluted with water and the product extracted with ethyl acetate. The organic phase is washed with brine, dried over magnesium sulphate and evaporated. The reissue is subjected to silica gel column chromatography (c-HEX/EtOAc=3:1) affording the desired product 2-Chloro-5-[1-(2-methyl-5-pentafluoroethyl-4-trifluoromethyl-2H-pyrazol-3-yl)-1H-[1,2,3]triazol-4-yl]-benzoic acid methyl ester (yield 53%).

$^1$H-NMR (400 MHz, CDCl$_3$): δ=8.47 (s, 1H), 8.12 (Is, 1H), 8.0 (d, 1H), 7.62 (d, 1H), 3.98 (s, 3H), 3.87 (s, 3H) ppm.

LC-MS RT 2.12, 504 (M+W), 545 (M+CH$_3$CN+H$^+$)

EXAMPLE 9 (Step 11)

Preparation of 2-Chloro-5-[1-(2-methyl-5-pentafluoroethyl-4-trifluoromethyl-2H-pyrazol-3-yl)-1H-[L2,3]triazol-4-yl]-benzoic acid (see Compound of Formula (III""))

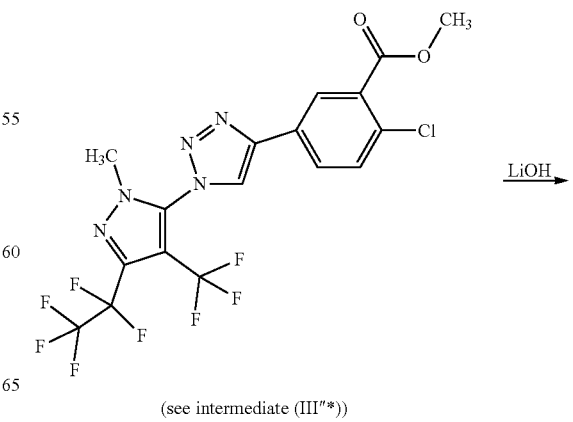

(see intermediate (III"*))

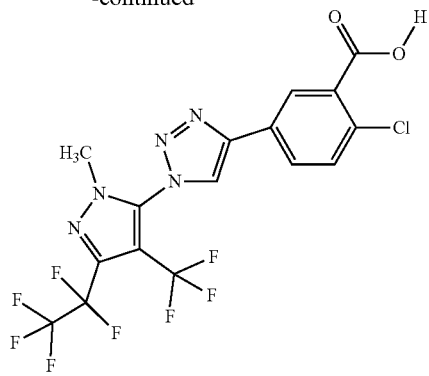

(see compound of formula (III''''))

2-Chloro-5-[1-(2-methyl-5-pentafluoroethyl-4-trifluoromethyl-2H-pyrazol-3-yl)-1H-[1,2,3]triazol-4-yl]-benzoic acid methyl ester (1.53 g, 3.0 mmol) is suspended in a mixture of water and tetrahydrofuran (1:3, 50 mL) and lithium hydroxide (0.22 g, 9.1 mmol) is added. The resulting mixture is stirred vigorously for 5 hours at 60° C. The reaction mixture is diluted with water and acidified with hydrogen chloride (2N). The aqueous phase is extracted twice with AcOEt, dried over MgSO$_4$ and concentrated under vacuum to afford the desired product 2-Chloro-5-[1-(2-methyl-5-pentafluoroethyl-4-trifluoromethyl-2H-pyrazol-3-yl)-1H-[1,2,3]triazol-4-yl]-benzoic acid. This compound was used without extra purification.

$^1$H-NMR (400 MHz, CDCl$_3$): δ=8.52 (s, 1H), 8.18 (Is, 1H), 8.09 (d, 1H), 7.66 (d, 1H), 3.88 (s, 3H) ppm.

LC-MS RT 2.08, 488 (M+H$^+$).

EXAMPLE 10 (Step 6)

Preparation of N-[4-chloro-3-(benzylcarbamoyl)phenyl]-1-methyl-3-(pentafluoroethyl)-4-(trifluoromethyl)-1H-pyrazole-5-carboxamide (Compound (IIa))

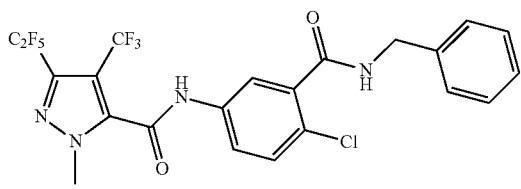

560 mg (1.79 mmol) of 1-methyl-3-pentafluoroethyl-4-trifluoromethylpyrazole-5-carboxylic acid were suspended in 10 ml of dichloromethane. The suspension was cooled to 0° C. and then subsequently admixed with 0.02 ml of N,N-dimethylformamide and 188 μl (2.15 mmol; 1.2 eq) oxalyl chloride. The reaction mixture was stirred firstly for 0.5 h at 0° C. and then for 3 hours at room temperature. The solvent was removed under reduced pressure on a rotary evaporator. The resulting 1-methyl-3-(pentafluoroethyl)-4-(trifluoromethyl)-1H-pyrazole-5-carbonyl chloride was used for the subsequent synthesis step without further work-up.

88.7 mg (0.34 mmol) of 5-amino-N-benzyl-2-chlorobenzamide, 2.77 mg (0.02 mmol) of N,N-dimethylpyridine-4-amine (DMPA) are dissolved in 2.5 ml of ethyl acetate. The solution is cooled to 0° C. using an ice bath and admixed with 119 μl (0.68 mmol) of N-ethyldiisopropylamine. 75.0 mg (0.22 mmol) of 1-methyl-3-(pentafluoroethyl)-4-(trifluoromethyl)-1H-pyrazole-5-carbonyl chloride are suspended in 2.5 ml of ethyl acetate and then added to the cooled reaction solution. The reaction mixture is heated for four hours at 50° C. and then stirred for 16 hours at room temperature. The reaction solution is diluted with 10.0 ml of ethyl acetate. The organic phase is washed three times with 1M hydrochloric acid, twice with 1M sodium hydroxide solution and once with saturated sodium chloride solution. The organic phase is dried over sodium sulphate and filtered and solvent is removed under reduced pressure on a rotary evaporator. This gives 140 mg (0.17 mmol) of N-[4-chloro-3-(benzylcarbamoyl)phenyl]-1-methyl-3-(pentafluoroethyl)-4-(trifluoromethyl)-1H-pyrazole-5-carboxamide (97%) as white solid.

$^1$H-NMR (400 MHz, d$_3$-acetonitrile): δ=9.29 (bs, 1H), 7.78 (d, 1H), 7.67 (dd, 1H), 7.48 (d, 1H), 7.21-7.52 (m, 6H), 4.54 (d, 2H), 3.97 (s, 3H) ppm.

HPLC-MS$^{a)}$: log P=3.90 mass (m/z)=555.1 [M+H]$^+$.

$^{a)}$Note regarding the determination of the log P values and mass detection: The log P values given were determined in accordance with EEC Directive 79/831 Annex V.A8 by HPLC (High Performance Liquid Chromatography) on a phase inversion column (C18). Agilent 1100 LC system; 50*4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 min, then 95% acetonitrile for a further 1.25 min; oven temperature 55° C.; flow: 2.0 ml/min. The mass detection is carried out via an Agilend MSD system.

$^1$ The stated mass is the peak of the isotope pattern of the [M+H]$^+$ ion with the highest intensity.

The invention claimed is:

1. Process for the synthesis of one or more 5-fluoro-1H-pyrazoles of formula (I)

wherein an olefin of formula (a)

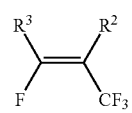

is reacted with water and a base, and
b) is reacted with a hydrazine of the formula (b)

wherein

R$^1$ is selected from C$_1$-C$_6$ alkyl, C$_5$-C$_{10}$ aryl, optionally C$_1$-C$_6$ alkyl, optionally methyl;

R$^2$ is a trihalomethyl moiety with at least one fluorine atom; and

R$^3$ is selected from C$_1$-C$_5$ haloalkyl.

2. Process according to claim 1, wherein
$R^1$ is methyl
$R^2$ is $CF_3$
$R^3$ is $C_2F_5$.

3. Process according to claim 1, wherein the base is triethylamine.

4. Process for the synthesis of one or more 5-fluoro-1H-pyrazoles of formula (I),

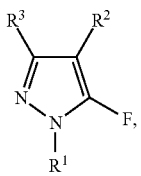
(I)

comprising reacting a compound of formula (c)

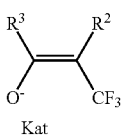
(c)

with a hydrazine of formula (b)

$$R^1\text{—NH—NH}_2 \quad (b),$$

wherein
$R^1$ is selected from $C_1$-$C_6$ alkyl, $C_5$-$C_{10}$ aryl;
$R^2$ is a trihalomethyl moiety with at least one fluorine atom; and
$R^3$ is selected from $C_1$-$C_5$ haloalkyl,
and wherein Kat is any organic or inorganic kation except from a proton.

5. Process according to claim 4, wherein
$R^2$ is trifluoromethyl,
$R^3$ pentafluoromethyl,
and wherein Kat is $(HNAlkyl_3)^+$.

6. Process for the preparation of a compound of formula (IV)

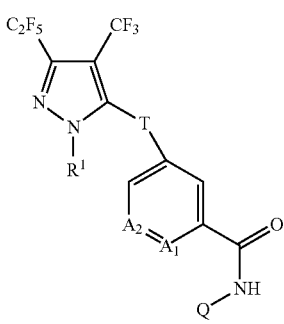
(IV)

in which
$R^1$ is $C_1$-$C_4$-alkyl; and
$A_1$ is C—$R^2$; and
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH-cyclopropyl); optionally hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, optionally hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, optionally hydrogen, fluorine, chlorine, bromine, optionally chlorine; and $A_2$ is C—$R^3$ or nitrogen; and
$R^3$ is hydrogen, methyl, fluorine or chlorine, optionally hydrogen; and T represents one of the groups T1-T9 listed below, where the bond to the pyrazole head group is marked with an asterisk *,

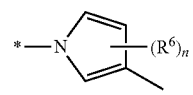
T1

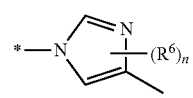
T2

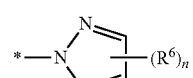
T3

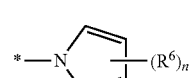
T4

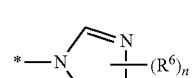
T5

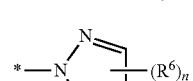
T6

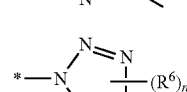
T7

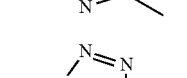
T8 or

*—C(=O)—NH—
T9; and $R^6$ independently of one another represents halogen, cyano, nitro, amino or optionally substituted $C_1$-$C_6$- alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, optionally 0, provided that n is 0 or 1 in T5, T6 and T8 and provided n is 0 in T7; and Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, optionally with one or two, optionally with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; optionally Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; optionally cyclopropyl, 1-cyanocyclopropyl or benzyl (—$CH_2$—$C_6H_5$);

comprising conducting the process according to claim 1.

7. Process according to claim 6, wherein a compound of formula (IV) is a compound of formula (II), optionally of formula (II').

8. Process according to claim 6, wherein a compound of formula (IV) is compound (IIa).

9. Process according to claim 6, further comprising:
reacting compound (I) with a cyano-donor to prepare intermediate of formula (6)

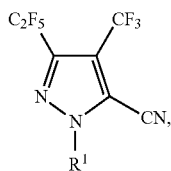

(6)

wherein $R^1$ is ($C_1$-$C_4$)-alkyl; and
reacting compound (6) with an inorganic strong base in a first hydrolysis followed by adding an inorganic acid in a second hydrolysis to prepare intermediate of formula (7)

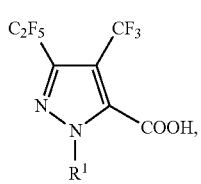

(7)

wherein
$R^1$ is ($C_1$-$C_4$)-alkyl; and
reacting a compound of formula (8) or a salt thereof (8') with an activated form (7') of compound (7)

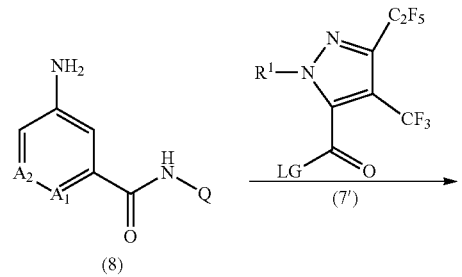

(8)

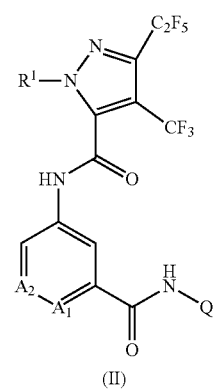

(II)

wherein LG is any leaving group, to prepare a compound of formula (II).

10. Process according to claim 6, wherein a compound of formula (IV) is a compound of formula (III)

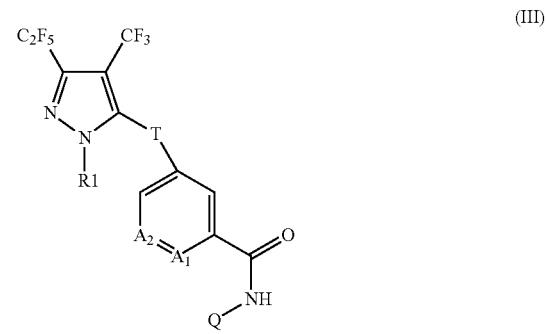

(III)

in which
$R^1$ is ($C_1$-$C_4$)-alkyl; and
$A_1$ is C—$R^2$;
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH-cyclopropyl); optionally hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, optionally hydrogen, fluorine, chlorine, bromine, CN, NO$_2$, methyl, fluoromethyl, difluoromethyl, trifluoromethyl, 2,2,2-trifluoroethyl, methoxy, ethoxy, or pentafluoroethoxy, optionally hydrogen, fluorine, chlorine, bromine, most optionally chlorine; and A$_2$ is C—R$^3$ or nitrogen;

R$^3$ is hydrogen, methyl, fluorine or chlorine, optionally hydrogen; and

Q is hydrogen, cyano, hydroxy, formyl or one of the groupings C$_1$-C$_6$-alkyl, C$_3$-C$_6$-alkenyl, C$_3$-C$_6$-alkynyl, C$_3$-C$_9$-cycloalkyl, C$_3$-C$_9$-heterocycloalkyl, C$_1$-C$_4$-alkoxy, C$_4$-C$_{15}$-alkylcycloalkyl, C$_4$-C$_{15}$-cycloalkylalkyl, C$_1$-C$_6$-hydroxyalkyl, C$_6$-aryl-C$_1$-C$_3$-alkyl, C$_5$-C$_6$-heteroaryl-C$_1$-C$_3$-alkyl, C$_1$-C$_4$-aminoalkyl, aminocarbonyl-C$_1$-C$_4$-alkyl or C$_1$-C$_4$-alkyl-amino-C$_1$-C$_4$-alkyl which are optionally substituted with one, two, three, four or five, optionally with one or two, optionally with one, substituents independently selected from the group consisting of hydroxy, nitro, amino, halogen, C$_1$-C$_3$-alkoxy, cyano, hydroxycarbonyl, C$_1$-C$_4$-alkoxycarbonyl, C$_1$-C$_4$-alkylcarbamoyl, C$_4$-C$_6$-cycloalkylcarbamoyl and optionally independently with one, two or three substituents selected from the group consisting of halogen, cyano, nitro, hydroxycarbonyl, C$_1$-C$_2$-alkylcarbamoyl, C$_1$-C$_2$-alkyl, halogenated C$_1$-C$_2$-alkyl and C$_1$-C$_2$-alkoxy substituted phenyl; optionally Q is C$_3$-C$_6$-cycloalkyl, or C$_3$-C$_6$-cycloalkyl which is substituted with at least one substituent selected from the group consisting of chlorine, fluorine, bromine, iodine, cyano and hydroxy, or C$_6$-aryl-C$_1$-C$_3$-alkyl; optionally cyclopropyl, 1-cyanocyclopropyl or benzyl (—CH$_2$—C$_6$H$_5$);

T represents one of the 5-membered heteroaromatics T1-T8 listed below, where the bond to the pyrazole head group is marked with an asterisk *,

T1

T2

T3

T4

T5

T6

T7

T8 wherein

R$^6$ independently of one another represents halogen, cyano, nitro, amino or optionally substituted C$_1$-C$_6$-alkyl, C$_1$-C$_6$-alkyloxy, C$_1$-C$_6$-alkylcarbonyl, C$_1$-C$_6$-alkylsulphanyl, C$_1$-C$_6$-alkylsulphinyl, C$_1$-C$_6$-alkylsulphonyl, and n represents the values 0-2, optionally 0, provided that n is 0 or 1 in T5, T6 and T8 and provided n is 0 in T7.

11. Process according to claim 10, wherein a compound of formula (III) is compound of formula (III'), optionally compound (IIIa) or compound (IIIb).

12. Process according to claim 10, further comprising reacting a compound of formula (I) with an intermediate of formula (11) by nucleophilic substitution of the fluoride at the ring position of a compound of formula (I)

wherein

R$^1$ is optionally halogenated (C$_1$-C$_4$)-alkyl or optionally halogenated cyclopropyl; and U represents bromine, iodine, triflate, boronic acid, boronic ester or trifluoroboronate; and the five-membered cycles of E$_1$-E$_3$, carbon and nitrogen represent the 5-membered heterocycles selected from the group consisting of

T1

T2

T3

T4

T5

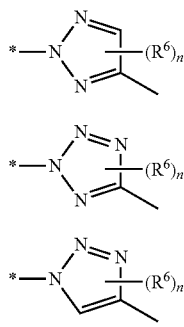

T6

T7

T8 wherein $R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, optionally 0, provided that n is 0 or 1 in T5, T6 and T8 and provided n is 0 in T7;

to prepare an intermediate of formula (12); and reacting a compound of formula (12) and a compound of formula (13)

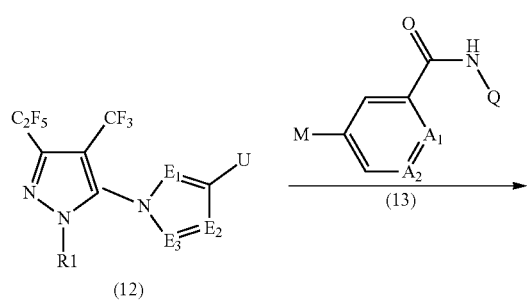

wherein $R^1$, $A_1$, $A_2$, and Q are as defined for a compound of formula (III) and U represents bromine, iodine, triflate, boronic acid, boronic ester or trifluoroboronate; and the five-membered cycles of $E_1$-$E_3$, carbon and nitrogen represent the 5-membered heterocycles selected from the group consisting of

T1

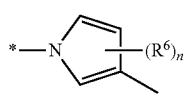

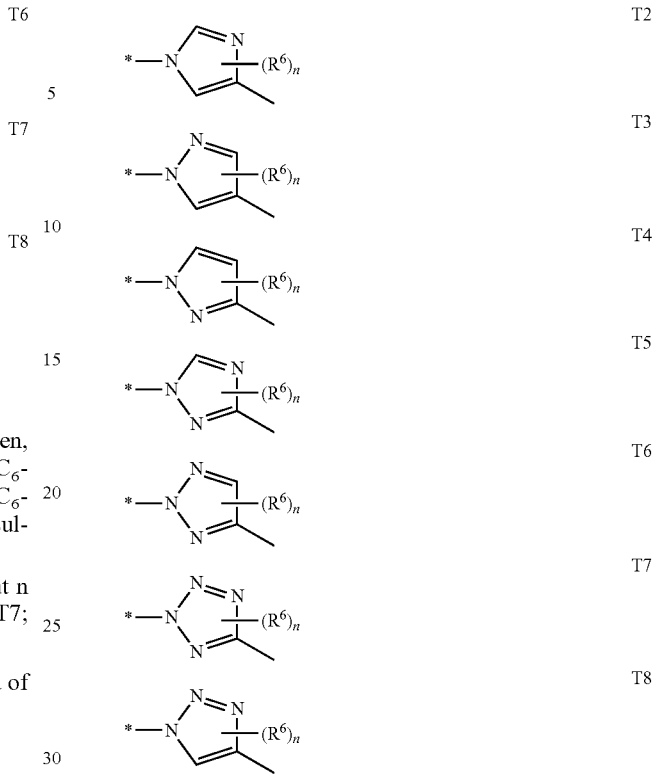

T2

T3

T4

T5

T6

T7

T8 wherein $R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, optionally 0, provided that n is 0 or 1 in T5, T6 and T8 and provided n is 0 in T7; and M represents bromine, iodine or triflate when U represents a boronic acid, boronic ester or trifluoroboronate; or M represents a boronic acid, boronic ester or trifluoroboronate when U represents bromine, iodine or triflate to prepare a compound of formula (III).

13. Process according to claim 6, wherein a compound of formula (IV) is a compound of formula (III"), optionally of formula (III''').

14. Process according to claim 13 further comprising a process wherein an olefin of formula (a)

(a)

is reacted with water and a base, and d) is reacted with a hydrazine of the formula (b)

(b), wherein

R¹ is selected from $C_1$-$C_6$ alkyl, $C_5$-$C_{10}$ aryl, optionally $C_1$-$C_6$ alkyl, optionally methyl;

R² is a trihalomethyl moiety with at least one fluorine atom; and

R³ is selected from $C_1$-$C_5$ haloalkyl, a) or b) further comprising reacting a compound of formula (I) and an azide-donoer to prepare intermediate (14)

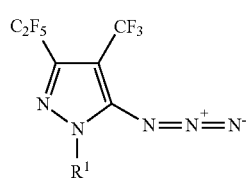

(14)

wherein R¹ is as defined for a compound of formula (III); and reacting intermediate (14) with an intermediate of formula (15) to give an intermediate (III"*)

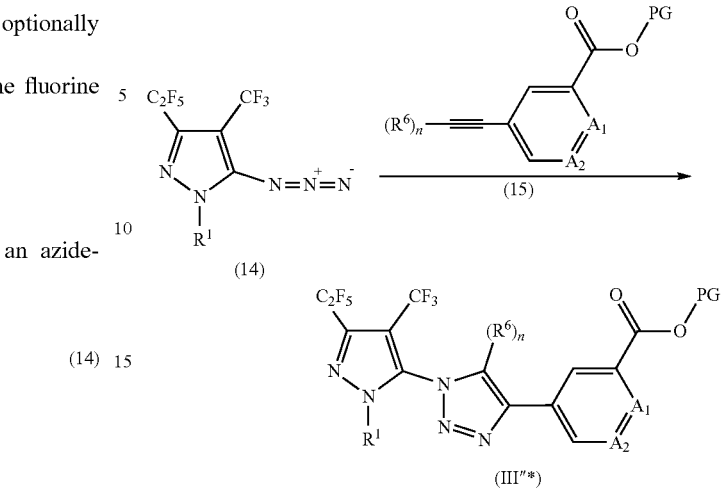

wherein R¹, R⁶, $A_1$, and $A_2$ are as defined for compound (III), n is 0 or 1 and PG is any protective group of the carboxylic group optionally $C_1$-$C_6$-alkyl (optionally methyl).

15. Process according to claim 1, wherein R¹ is methyl.

* * * * *